United States Patent
Braxmeier et al.

(10) Patent No.: US 7,998,945 B2
(45) Date of Patent: Aug. 16, 2011

(54) METHODS FOR THE TREATMENT AND AMELIORATION OF ATOPIC DERMATITIS

(75) Inventors: Tobias Braxmeier, Dresden (DE); Tim Friedrichson, Dresden (DE); Gary Jennings, Dresden (DE)

(73) Assignee: Jado Technologies GmbH, Dresden (DE)

( * ) Notice: Subject to any disclaimer, the term of this patent is extended or adjusted under 35 U.S.C. 154(b) by 113 days.

(21) Appl. No.: 12/158,615

(22) PCT Filed: Dec. 20, 2006

(86) PCT No.: PCT/EP2006/012322
§ 371 (c)(1),
(2), (4) Date: Sep. 18, 2008

(87) PCT Pub. No.: WO2007/071402
PCT Pub. Date: Jun. 28, 2007

(65) Prior Publication Data
US 2009/0018105 A1    Jan. 15, 2009

Related U.S. Application Data

(60) Provisional application No. 60/855,129, filed on Oct. 30, 2006.

(30) Foreign Application Priority Data

Dec. 23, 2005 (EP) .................................. 05028388

(51) Int. Cl.
*A61K 31/452* (2006.01)
*A61K 31/661* (2006.01)

(52) U.S. Cl. ......................................... 514/76; 514/315
(58) Field of Classification Search .................. None
See application file for complete search history.

(56) References Cited

U.S. PATENT DOCUMENTS
5,703,063 A    12/1997    Chasalow

FOREIGN PATENT DOCUMENTS
WO    WO 2006/002422    1/2006

OTHER PUBLICATIONS

Uenishi et al., Journal of Dermatology (Feb. 2003), 30(2), pp. 91-97 (abstract).*
International Search Report for PCT International Application PCT/EP2006/012322, mailed Apr. 11, 2007 (4 pgs.).
Grosman N., "Effect of the Anti-Neoplastic Agents Edelfosine (ET-18-OCH3), ILMOFOSINE (BM 41.440) and the Hexadecylphosphocholine Analoges D-20133 and D-21266 on Histamine Release from Isolated Rat Mast Cells", *Immunopharmacology*, vol. 44, No. 3, 1999, pp. 211-221. (XP008061676).
Mazer et al., "Dose-Dependent Agonist and Antagonist Effects of the Platelet-Activating Factor Analogue 1-Palmitoyl-2-Acetoyl-Sn-Gylcero-3-Phosphocholine on B Lymphocytes" *Journal of Allergy and Clinical Immunology*, vol. 102, No. 2, Aug. 1998, pp. 231-237. (XP005687525).

* cited by examiner

Primary Examiner — Phyllis G. Spivack
(74) Attorney, Agent, or Firm — Foley & Lardner LLP

(57) ABSTRACT

The present invention relates to a method for the treatment and/or amelioration of atopic dermatitis, the method including the administration of a pharmaceutically active dose of a compound selected from miltefosine, edelfosine, perifosine and ilmofosine to a subject in need of such a treatment and/or amelioration.

3 Claims, 7 Drawing Sheets

METHODS FOR THE TREATMENT AND AMELIORATION OF ATOPIC DERMATITIS

The present invention relates of the use of certain inner ionic (zwitter ionic) phospholipids, phosphonolipids and phosphate derivatives for the preparation of a pharmaceutical composition for the treatment, prevention and/or amelioration of an immunological disorder related to mast cell sensitization and/or activation. Preferred in this context are Edelfosine, Miltefosine and Perifosine. In a particularly preferred embodiment, the present invention relates to the use of Miltefosine for the preparation of a pharmaceutical composition for the treatment, prevention and/or amelioration of allergic diseases, in particular acute hyperallergic diseases, like asthma, atopic dermatitis and mastocytosis.

Atopic diseases account for a large proportion of health care spending in industrialized countries, as these conditions are common, persistent and currently incurable. Current therapies for asthma and rhinitis are more or less effective in most patients, whereas treatment for atopic dermatitis typically shows little effect. Anaphylactic shock is considered to be treatable with epinephrine but there is a search for preventive therapies for susceptible patients. Therefore, there is a need for new pharmaceutical interventions to deal with disorders related to mast cell sensitization and/or activation, like more severe asthma that is not well controlled by high doses of inhaled corticosteroids. Furthermore, a need for a safe medication that would be effective in all atopic diseases is desired, as they often occur together.

Approximately 10% of the world population suffer from allergies. Of the 40 million allergy sufferers in the United States, about 9.9 million have asthma. Additionally, 35% of the population suffers from allergic rhinitis ("hay fever"), 15% from urticaria, 15% from eczema, and 1% from anaphylaxis. Asthma is the most frequent chronic condition for those under age 18. These disorders can cause lost work and an impaired quality of life, and in the case of asthma and anaphylaxis, can be fatal. Clinically, asthma is recognized by airway hyperactivity and reversible airways obstruction. Pathological derangements at the tissue level include constriction of airway smooth muscle, increased vascular permeability resulting in edema of airways, outpouring of mucus from goblet cells and mucus glands, parasympathetic nervous system activation, denudation of airway epithelial lining cells, and influx of inflammatory cells. The early phase of the asthmatic reaction is mediated by histamine and other mast cell mediators that induce rapid effects on target organs, particularly smooth muscle.

Mastocytosis is a very heterogeneous group of disorders characterized by an abnormal accumulation of mast cells in different tissues, mainly in the skin (cutaneous mastocytosis or urticaria, like urticaria pigmentosa) and the bone marrow, but also in spleen, liver, lymph nodes, and the gastrointestinal tract, depending on the nature of the disease (systemic mastocytosis). They can affect humans of either sex at any age. Mastocytoses are usually acquired diseases, but some rare familial cases have been described.

Classical allergic reactions or "immediate hypersensitivity" (type I) reactions occur within 15 minutes following interaction of soluble antigen with mast cells. The pathology is related to mast cell degranulation, and the reaction is driven by mast cell mediators such as histamine and leukotriene C4. An example of an in vivo counterpart is an urticarial reaction following injection of penicillin in a penicillin-allergic patient Mast cell activation is thus the central event in allergic inflammation and most allergic diseases are caused by IgE (immunoglobulin E)-mediated hypersensitivity reactions. Allergic individuals synthesize IgE in response to foreign substances known as allergens. IgE antibodies are specific to the allergen to which they are elicted. The IgE antibodies bind to IgE receptors on the surface of mast cells in tissues and basophilic granulocytes in the blood. A polyvalent allergen can crosslink the surface-bound IgE, leading to degranulation of the cells. This process results in the release of pharmacologically active agents such as histamines and prostaglandins, which in turn cause the allergic symptoms in the target organ, e.g., bronchospasm in asthma or edema in a local allergic reaction. Thus, a central cell in most common allergies is the mast cell, and a central molecule is IgE.

Mast cells are specialized hematopoietic cells that are derived from progenitor stem cells in the bone marrow that play an important role in immediate (type I) hypersensitivity and inflammatory reactions by secreting a large variety of chemical mediators from storage sites in their granules upon stimulation. Mast cells are characterized by their heterogeneity, not only regarding tissue location and structure but also at the functional and histochemical levels. In inflammatory disorders, such as allergies and asthma, increased numbers of mast cells in affected tissues have been documented with a positive correlation between mast cell number and the severity of the allergic response symptoms. In systemic mastocytosis with multiple organs involvement, infiltrates of mast cells in tissues are formed by clusters of mast cells in portal areas of liver, perifollicular of spleen, perivascular of skin or in sinus of lymph nodes. Hepatomegaly and splenomegaly have been observed in 50% of patients with systemic mastocytosis.

The role for which mast cells are best known is that in mediating IgE-triggered allergic reactions. Mast cells, and their circulating counterparts the basophils, possess high-affinity receptor for IgE known as FcεRI, which after binding IgE can be stimulated by crosslinking to release a variety of biologically active mediators such as histamine, proteoglycans, proteases, serotonin. The event that initiates immediate hypersensitivity in mast cells and basophiles is binding of antigen to receptor bound IgE on the cell surface. Furthermore, crosslinking of IgE receptors induces synthesis and release of prostaglandins, leukotrienes and cytokines. The FcεRI γ-chains contain immunoreceptor tyrosine-based activation motifs (ITAMs), and signaling pathways originating at the FcεRI are similar to those generated through activation of other immunoreceptors that contain ITAMs. In brief, upon FcεRI cross-linking, the src family kinase lyn phosphorylates the ITAM, to which syk kinase is recruited. Syk becomes activated, and phosphorylates a variety of downstream, in particular cytosolic, target proteins.

Mast cells may also be activated by mechanisms other than cross-linking FcεRI, such as in response to mononuclear phagocyte-derived chemocytokines, to T cell-derived cytokines and to complement-derived anaphylatoxins. Mast cells may also be recruited and activated by other inflammatory cells or by neurotransmitters which serves as links to the nervous system. Upon activation, mast cells release a variety of mediators, which give rise to increased vascular permeation, vasodilation, bronchial and visceral smooth muscle contraction, and local inflammation. In the most extreme form of immediate hypersensitivity reaction known as anaphylaxis, mediators released from mast cells can restrict airways to the point of asphyxiation. So-called atopic individuals, who are prone to develop strong immediate hypersensitivity responses, may suffer from asthma, hay fever or chronic eczema. These individuals possess higher than average plasma IgE levels. Antigen-induced cell activation can be simulated by polyvalent anti-IgE or by anti-FcεRI antibodies. Such antibodies can activate mast cells from atopic as well as non-atopic individuals, whereas allergens activate mast cells only in atopic persons.

In mastocytosis, symptomatic release of mast cells granules may be triggered by emotional disturbance, fever, fatigue, physical stimuli (heat, cold, friction, exercise, sunlight), exposure to ethanol, medicaments, like aspirin, opiates, anticholinergics, non-steroidal anti-inflammatory drugs (aspirin), anesthetics, narcotics, antibiotics, bacterial toxins, pesticides, viral, bacterial or fungal infection, mold, venoms, biologic polypeptides (lobster, crayfish, jellyfish), certain foods, food colorings or flavorings, preservatives or perfumes.

Allergy medication should either prevent the release of granular components such as histamine from mast cells, or block the response of tissues to histamine. Most of the currently available medications are anti-histamines (histamine H-1 receptor antagonists) diminishing the effects of histamine on tissue by blocking of histamine receptors. They do not prevent the production or release of histamine, which is responsible for many but not all symptoms of allergy.

A number of inflammatory mediators other than histamine, such as leukotrienes and a number of vasoactive cytokines, are also released by mast cells and basophils. These pro-inflammatory mediators remain unaffected by anti-histamines and contribute significantly to the pathophysiology of allergy and asthma. Sometimes a combination of anti-allergic and anti-inflammatory drugs works better, but at the same time these combinations cause adverse side effects. In more severe allergic reactions (anaphylaxis), anti-histamines do not have a therapeutic effect. In mastocytosis, conventional treatments for urticaria pigmentosa have been relatively ineffective. Antihistamines may attenuate some of the symptoms, but aspirin and codeine degranulate mast cells and may aggravate symptoms.

The influence of certain ether lipids and ether phospholipids on histamine release from isolated rat mast cells has been investigated. Depending on the application conditions, some of these compounds were found to enhance or inhibit antigen-induced histamine release. These studies were carried out in order to investigate the mechanism of toxicity of antineoplastic ether phospholipids towards cancer cells based on the hypothesis that the ether phospholipids stimulate the activation of macrophage functions. Accordingly, cancer treatment was discussed as a potential application of these compounds. See, Grosman, Immunopharmacology 1990, 20, 143-149; Grosman, Immunopharmacology 1999, 44, 211-221; Grosman, Inflamm. Res., Supplement 12002, S05-S06. Yet, the data provided by Grosman are not conclusive and a high variation of immunomodulation in potential cancer treatment is described, depending on the experimental set-up.

Compounds that specifically impair mast cell degranulation are assumed to be of low toxicity because regulated exocytosis is not a vital function of mast cells, leaving them available to participate in other aspects of immune function. In humans, mast cell exocytosis has little or no utility in persons living in developed countries. IgE-mediated immunity appears to have evolved primarily to function in defense against parasitic infestation. Such infestations are rare in Western societies, and mast cell degranulation is now observed almost exclusively as part of dysfunctional allergic reactions. Therefore, blockage of mast cell degranulation per se is effective in preventing allergic inflammation and has few undesirable consequences.

A limited number of pharmacologic agents has been tested for effects on mast cell activation. Such "mast cell stabilizers" in use today include cromolyn sodium (Gastrocrom®) or Ketotifen (Apo®-Ketotifen, Zaditen®), nedocromil and lodoxamide. Cromolyn sodium is a broad based medication that was empirically found to reduce mast cell secretion, and is now thought to work by inactivating chloride channels, however, it has low efficacy. Several novel agents have been tested for inhibition of mast cell degranulation during the last years. Examples include tryptase inhibitors (He et al., J. Pharmacol. Exp. Ther. 2004, 309(1), 119-126), chymase inhibitors (He et al. J. Pharmacol. Exp. Ther. 1999, 291, 517-523), and idandones (Frankish et al. J. Pharm. Pharmacol. 2004, 56, 1423-1427). While some have shown encouraging results, none of these agents is approved for clinical use and it is rather unclear, if they will ever make it to the clinical stage.

In view of the aforementioned drawbacks to currently available therapies, there is an ongoing need in the field for therapeutic agents and methods to combat mast cell related disorders, like allergies.

According to the present invention, a solution to this technical problem is achieved by providing the use of a compound of the following formula I

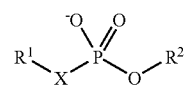

I wherein
$R^1$ is a $C_{4-13}$ hydrocarbon group comprising a quarternary nitrogen atom;
X is O or a direct bond;
$R^2$ is a $C_{10-20}$ hydrocarbon group, wherein one or more hydrogens are optionally replaced by fluorine and wherein one or more $CH_2$ groups are optionally replaced by oxygen, or a group of the following formula II

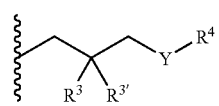

II

Y is O, O(CO), S or S(CO);
$R^3$ is OH, $C_{1-4}$ alkyl, O—$C_{1-3}$ alkyl, O(CO)NH—$C_{1-3}$ alkyl, O(CO)—$C_{1-6}$ alkyl, S(CO)—$C_{1-6}$ alkyl, O(CO)—$C_{2-3}$ alkenyl or $CH_2O$—$C_{1-3}$ alkyl;
$R^{3'}$ is H or $C_{1-4}$ alkyl; and
$R^4$ is a $C_{10-20}$ hydrocarbon group, wherein one or more hydrogens are optionally replaced by fluorine,
for the preparation of a pharmaceutical composition for the treatment, prevention and/or amelioration of an immunological disorder related to mast cell sensitization and/or activation.

The lipid bilayer that forms cell membranes is a two dimensional liquid the organization of which has been the object of intensive investigations for decades by biochemists and biophysicists. Although the bulk of the bilayer has been considered to be a homogeneous fluid, there have been repeated attempts to introduce lateral heterogeneities, lipid microdomains, into our model for the structure and dynamics of the bilayer liquid (Glaser, Curr. Opin. Struct. Biol. 3 (1993), 475-481; Jacobson, Comments Mol. Cell. Biophys. 8 (1992), 1-144; Jain, Adv. Lipid Res. 15 (1977), 1-60; Winchil, Curr. Opin. Struct. Biol. 3 (1993), 482-488.

The realization that epithelial cells polarize their cell surfaces into apical and basolateral domains with different protein and lipid compositions in each of these domains, initiated a new development that led to the "lipid raft" concept (Simons, Biochemistry 27 (1988), 6197-6202; Simons, Nature 387 (1997), 569-572). The concept of assemblies of sphingolipids and cholesterol functioning as platforms for membrane proteins was promoted by the observation that these assemblies survived detergent extraction, and are referred to as detergent resistant membranes, DRM (Brown, Cell 68 (1992), 533-544). This was an operational break-through where raft-association was equated with resistance to Triton-X100 extraction at 4° C. The addition of a second criterion, depletion of cholesterol using methyl-β-cyclodextrin (Ilangumaran, Biochem. J. 335 (1998), 433-440; Scheiffele, EMBO J. 16 (1997), 5501-5508) leading to loss of detergent resistance, prompted several groups in the field to explore the role of lipid microdomains in a wide spectrum of biological reactions. There is now increasing support for a role of lipid assemblies in regulating numerous cellular processes including cell polarity, protein trafficking and signal transduction.

Cell membranes are two-dimensional liquids. Thus, lateral heterogeneity implies liquid-liquid immiscibility in the membrane plane. It has been well known that hydrated lipid bilayers undergo phase transitions as a function of temperature. These transitions, which occur at defined temperatures for each lipid species, always involve some change in the order of the system. The most important of these transitions is the so-called "main" or "chain-melting" transition in which the bilayer is transformed from a highly ordered quasi-two dimensional crystalline solid to a quasi-two dimensional liquid. It involves a drastic change in the order of the systems, in particular of the translational (positional) order in the bilayer plane and of the conformational order of the lipid chains in a direction perpendicular to this plane. Translational order is related to the lateral diffusion coefficient in the plane of the membrane and conformational order is related to the trans/gauche ratio in the acyl chains. The main transition has been described as an ordered-to-disordered phase transition, so that the two phases may be labeled as solid-ordered ($s_o$) below the transition temperature and liquid-disordered ($I_d$) above that temperature. Cholesterol and phopholipids are capable of forming a liquid-ordered ($I_o$) phase that can coexist with a cholesterol-poor liquid-disordered ($I_d$) phase thereby permitting phase coexistence in wholly liquid phase membranes (Ipsen, Biochem. Biophys. Acta 905 (1987) 162-172; Ipsen, Biophys. J. 56 (1989), 661-667). Sterols do so as a result of their flat and rigid molecular structure, which is able to impose a conformational ordering upon a neighboring aliphatic chain (Sankaram, Biochemistry 29 (1990), 10676-10684), when the sterol is the nearest neighbor of the chain, without imposing a corresponding drastic reduction of the translational mobility of the lipid (Nielsen, Phys. Rev. E. Stat. Phys. Plasmas Fluids Relat. Interdiscip. Topics 59 (1999), 5790-5803). Due to the fact that the sterol does not fit exactly in the crystalline lattice of an $s_o$ (gel) lipid bilayer phase it will, if it dissolves within this phase, disrupt the crystalline translational order without, however, significantly perturbing the conformational order. Thus, cholesterol at adequate molar fractions can convert $I_d$ or $s_o$ lipid bilayer phases to liquid-ordered ($I_o$) phases.

Lipid rafts are lipid platforms of a special chemical composition (rich in sphingomyelin and cholesterol in the outer leaflet of the cell membrane) that function to segregate membrane components within the cell membrane. Rafts are understood to be relatively small (30-50 nm in diameter, estimates of size varying considerably depending on the probes used and cell types analysed) but they can be coalesced under certain conditions. Their specificity with regard to lipid composition is reminiscent of phase separation behavior in heterogeneous model membrane systems. In fact, many of their properties with regard to chemical composition and detergent solubility are similar to what is observed in model systems composed of ternary mixtures of an unsaturated phosphatidylcholine, sphingomyelin (or a long-chain saturated phosphatidylcholine), and cholesterol (de Almeida, Biophys. J. 85 (2003), 2406-2416). Rafts may be considered domains of a $I_o$ phase in a heterogeneous I phase lipid bilayer composing the plasma membrane. What the other coexisting phase (or phases) is (or are) is not clear at present. There is consensus that the biological membrane is a liquid, so $s_o$ phase coexistence may be ignored for most cases. Whether the other phase (phases) is (are) $I_d$ or $I_o$ phases will depend upon the chemical identity of the phospholipids that constitute this phase (these phases) and the molar fraction of cholesterol in them. Rafts may be equated with a liquid-ordered phase and refer to the rest of the membrane as the non-raft liquid phase. Within the framework of thermodynamics, a phase is always a macroscopic system consisting of large number of molecules. However, in lipid bilayers the phases often tend to be fragmented into small domains (often only a few thousand molecules) each of which, per se, may not have a sufficient number of molecules to strictly satisfy the thermodynamic definition of a phase. The liquid-ordered raft phase thus comprises all the domains (small or clustered) of the raft phase in the membranes. The rest of the membrane surrounding the rafts, the liquid phase, may be a homogeneous percolating liquid phase or may be further subdivided into liquid domains not yet characterized.

Pralle, J. Cell. Biol. (2000) 148, 997-1008 employed photonic force microscopy to measure the size of lipid rafts and found that rafts in the plasma membrane of fibroblasts diffuse as assemblies of 50 nm diameter, corresponding to a surface area covered by about 3,000 sphingolipids. Based on data from cultured baby hamster kidney (BHK) cells, whose lipid composition and organelle surface area have been examined in detail, it appears that an individual cell has a surface area of approximately 2,000 $\mu m^2$. The lipid composition of the cell plasma membrane contains 26% phosphatidylcholine, 24% sphingomyelin, and 12% glycosphingolipids. Due to the asymmetric nature of the lipid organization in the plasma membrane, most of the sphingolipids occupy the outer leaflet of the bilayer, while less than half of the phosphatidylcholine has been estimated to be in this leaflet.

Assuming that most of the sphingolipid is raft-associated, rafts would cover more than half of the cell surface. The density of membrane proteins has been estimated to be around 20,000 molecules per $\mu m^2$. Thus, the plasma membrane would accordingly contain about $40 \times 10^6$ protein molecules. The number of 50-nm rafts would be about $10^6$, and if the density of proteins is the same in rafts as in the surrounding bilayer, each raft would carry about 20 protein molecules. If BHK cells are representative, it follows that the density of rafts floating in the fibroblast plasma membrane is high. If $20 \times 10^6$ raft protein molecules were distributed more or less randomly, each raft would likely contain a different subset of proteins. A kinase attached to the cytosolic leaflet of a raft is, therefore, unlikely to meet its substrate in the same individual raft. The small size of an individual raft may be important for keeping raft-borne signaling proteins in the "off" state. Accordingly, for activation to occur, many rafts have to cluster together, forming a larger platform, where the protein participants in a signal transduction process can meet, undisturbed by what happens outside the platform. Thus, rafts are small, and, when activated, they cluster to form larger platforms in which functionally related proteins can interact.

One way to analyze raft association and clustering is to patch raft and nonraft components on the surface of living cells by specific antibodies (Harder, J. Cell Biol. 141 (1998), 929-942; Janes, Semin. Immunol. 12 (2000), 23-34). If two raft components are cross-linked by antibodies, they will form overlapping patches in the plasma membrane. However, patching of a raft protein and a nonraft marker such as the transferrin receptor leads to the formation of segregated patches. Co-patching of two raft components is dependent on the simultaneous addition of both antibodies to the cells. If antibodies are added sequentially, segregated patches predominate. Notably, the patching behavior is cholesterol-dependent. As a consequence of the small size and the heterogeneous composition of individual rafts, these structures must be clustered in specific ways if signaling is to ensue.

One example of such a raft clustering process encountered in daily clinical practice is the IgE signaling during the allergic immune response (Sheets, Curr. Opin. Chem. Biol. 3 (1999), 95-99; Holowka, Semin. Immunol. 13 (2001), 99-105). The allergen that elicits the allergic reaction by stimulating the degranulation of a mast or basophilic cell is multivalent, binding several IgE antibody molecules. Cross-linking of two or more IgE receptors (FceRI) increases their association with rafts, as measured by increased detergent resistance. Within the rafts, cross-linked FceRI becomes tyrosine phosphorylated by raft-associated Lyn, a double-acylated Src-related kinase. The FceRI phosphorylation recruits the tyrosine kinase Syk, which is activated and in turn phosphorylates downstream signaling and scaffolding molecules finally leading to the formation of a signaling platform. This structure includes the raft protein LAT (linker of activation of T cells), which guides the clustering of additional rafts into the expanding platform (Rivera, Int. Arch. Allergy Immunol. 124 (2001), 137-141). Signaling leads to calcium mobilization, which triggers the release of preformed mediators such as histamine from the intracellular stores. The more participants are collected into the raft platform, the higher the signaling response. Uncontrolled amplification of the signaling cascade by raft clustering might trigger hyperactivation, with life-threatening consequences such as Quinke edema and allergic shock. The whole signaling assembly can be dissociated by dephosphorylation or down-regulated by internalization of the components by endocytosis (Xu, J. Cell Sci. 111 (1998), 2385-2396). Thus, in IgE receptor signaling, lipid rafts serve to increase the efficiency by concentrating the participating proteins and lipid into fluid microdomains and limiting their lateral diffusion so that proteins remain at the site of signaling. Even a small change of partitioning into lipid rafts can, through amplification, initiate a signaling cascade or prompt a deleterious overshoot, as occurs in allergic reactions (Kholodenko, Trends Cell Biol. 10 (2000), 173-178).

In the context of the present invention, it was surprisingly found that certain inner ionic phospholipids, phosphonolipids and phosphate derivatives, like Edelfosine, Miltefosine, Perisfosine, Ilmeofosine, Ilmofosine, 1-O-palmitoyl-2-O-methyl-sn-glycero-3-phosphocholine and 1-O-palmitoyl-2-O-ethyl-sn-glycero-3-phosphocholine, are potent inhibitors of mast-cell degranulation or function as mast cell stabilizers. In particular, it was surprisingly found that the compounds as disclosed herein can therapeutically be used in the treatment, prevention and/or amelioration of disorders related to mast cell sensitization and/or activation, in particular immunological disorders related to mast cell degranulation.

Accordingly, the present invention provides for the use of a compound of the following formula I

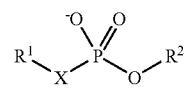

I for the preparation of a pharmaceutical composition for the treatment, prevention and/or amelioration of an immunological disorder related to mast cell sensitization and/or activation.

$R^1$ is a $C_{4-13}$ hydrocarbon group comprising a quarternary nitrogen atom. Preferably, $R^1$ is a group of one of the following formulae IIIa to IIIc:

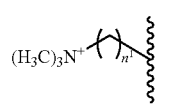

IIIa

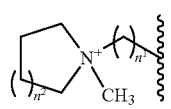

IIIb

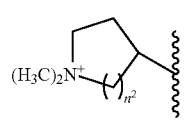

IIIc $n^1$ is an integer from 1 to 7, preferably from 2 to 6, more preferably $n^1$ is 2. $n^2$ is an integer of 1 or 2.

X is O or a direct bond. Preferably, X is O.

In one embodiment, $R^2$ is a $C_{10-20}$ hydrocarbon group, wherein one or more hydrogens are optionally replaced by fluorine and wherein one or more (preferably one or two) $CH_2$ groups are optionally replaced by oxygen. Preferably, $R^2$ is a $C_{10-20}$ hydrocarbon group including one or more (e.g. two, three or four) double bonds or a $C_{10-20}$ alkyl group. In a preferred embodiment, $R^2$ is a $C_{10-20}$ alkylene group or a $C_{10-20}$ alkyl group. More preferably, $R^2$ is a $C_{12-18}$ alkyl group.

In an alternative embodiment, $R^2$ is a group of the following formula II

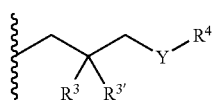

II

Y is O, O(CO), S, S(CO). Preferably, Y is O.

$R^3$ is OH, $C_{1-4}$ alkyl, O—$C_{1-3}$ alkyl, O(CO)NH—$C_{1-3}$ alkyl, O(CO)—$C_{1-6}$ alkyl, S(CO)—$C_{1-6}$ alkyl, O(CO)—$C_{2-3}$ alkenyl or $CH_2O$—$C_{1-3}$ alkyl. In one embodiment, $R^3$ is OH, O—$C_{1-3}$ alkyl, O(CO)NH—$C_{1-3}$ alkyl, O(CO)—$C_{1-6}$ alkyl, S(CO)—$C_{1-6}$ alkyl, O(CO)—$C_{2-3}$ alkenyl or $CH_2O$—$C_{1-3}$ alkyl. Preferably, $R^3$ is O($C_{1-2}$ alkyl) or OCONHCH$_3$. O(CO)—$C_{1-6}$ alkyl is another preferred $R^3$ group. More preferably, $R^3$ is O($C_{1-2}$ alkyl).

$R^{3'}$ is H or $C_{1-4}$ alkyl, preferably H or CH$_3$. In one embodiment, $R^{3'}$ is H.

$R^4$ is a $C_{10-20}$ hydrocarbon group, wherein one or more hydrogens are optionally replaced by fluorine. Preferably, $R^4$ is a $C_{10-20}$ hydrocarbon group including one or more (e.g. two, three or four) double bonds or a $C_{10-20}$ alkyl group. More preferably, $R^4$ is a $C_{12-18}$ alkyl group.

In a further alternative embodiment, $R^2$ is a group of the following formula IV or the following formula V:

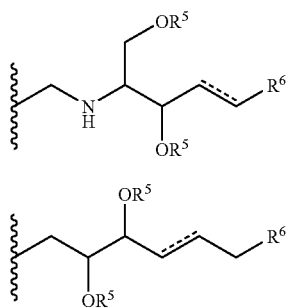

⹀ is used to represent a single bond or a double bond.

Each $R^5$ is independently selected from H and $C_{1-3}$ alkyl. Preferably, in a group of the formula IV or V one $R^5$ is H, while the other $R^5$ is $CH_3$.

$R^6$ is a $C_{9-15}$ hydrocarbon group, wherein one or more hydrogens are optionally replaced by fluorine. Preferably, $R^6$ is a $C_{11-13}$ alkyl group The general formulae given in the present invention are intended to cover all possible stereoisomers and diastereomers of the indicated compounds. In compounds comprising a group of the formula II, the stereochemistry, which is prevalent in naturally occurring glycerophospholipids, is preferred. In compounds comprising a group of the general formula IV or V, the stereochemistry present in naturally occurring sphingosine is preferred.

Table 1 shows compounds 1 to 21 and 23 to 28 which are preferred examples of compounds of formula I.

TABLE 1

| | Structure | Name and commercial source |
|---|---|---|
| 1 | 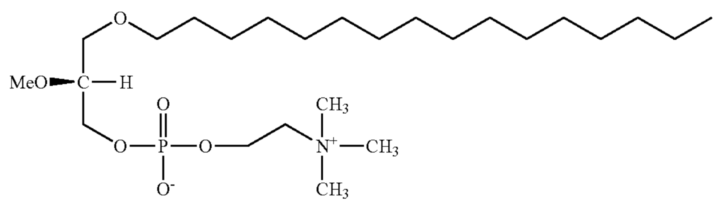 | 2-O-methyl PAF C-16; Cayman 60902 |
| 2 | 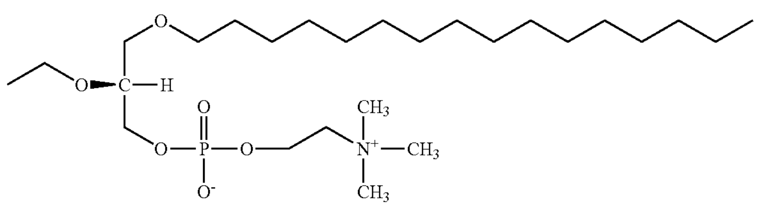 | 2-O-ethyl PAF C-16; Cayman 60925 |
| 3 | 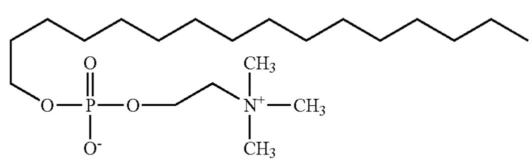 | Miltefosine (1-hexadecylphosphoryl-choline, HePC); Calbiochem 475841 |
| 4 | 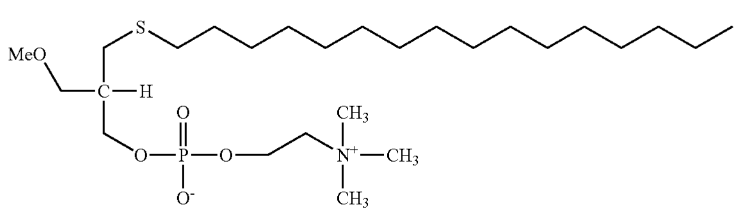 | Ilmofosine (1-hexadecylmercapto-2-methoxymethyl-3-propyl phosphoric acid monocholine ester); Sigma I2409 |
| 5 | 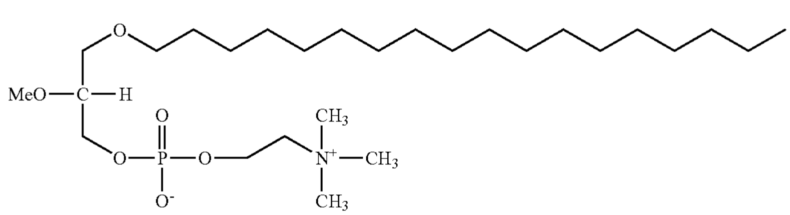 | Edelfosine (18:0-1:0 Diether PC); Calbiochem 341207, Sigma E1779 |

TABLE 1-continued

| # | Structure | Name and commercial source |
|---|---|---|
| 6 | 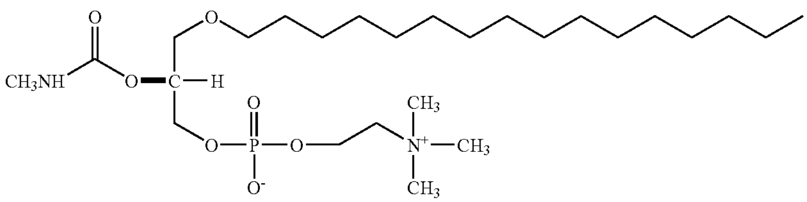 | mcPAF C-16 (1-O-palmitoyl-2-(N-methyl-carbamyl)-sn-glycero-3-phosphocholine); Sigma H4648 |
| 7 | 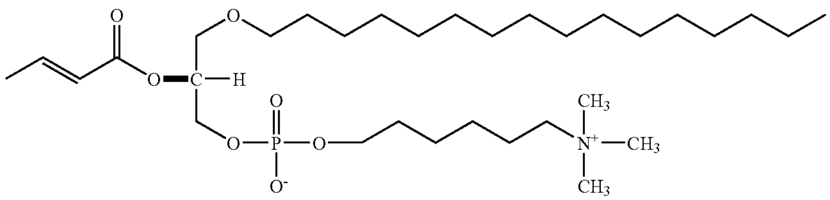 | butenoyl PAF C-16; Cayman 60929 |
| 8 | 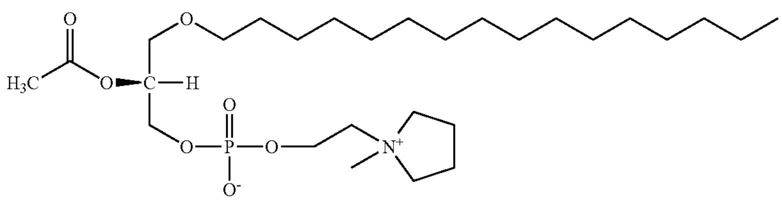 | pyrrolidino PAF C-16, Cayman 60909 |
| 9 | 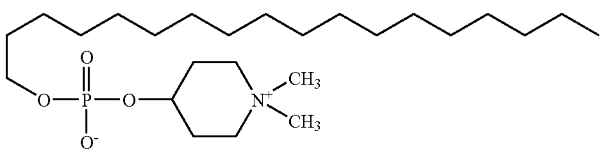 | Perifosine (octadecyl-(N,N-dimethyl-piperidinio-4-yl)-phosphate); Asta Medica D-21266 |
| 10 | 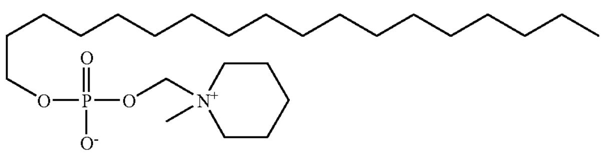 | octadecyl-(2-(N-methyl-piperidinio)-ethyl)-phosphate; Asta Medica D-20133 |
| 11 | 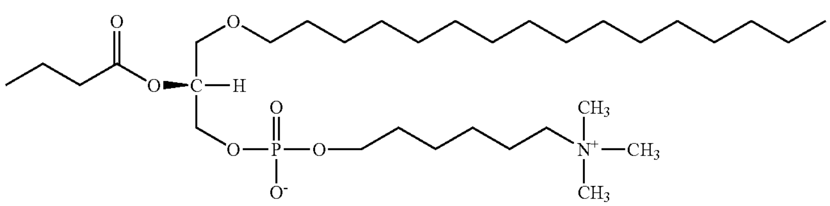 | butanoyl PAF C-16; Cayman 60928 |
| 12 | 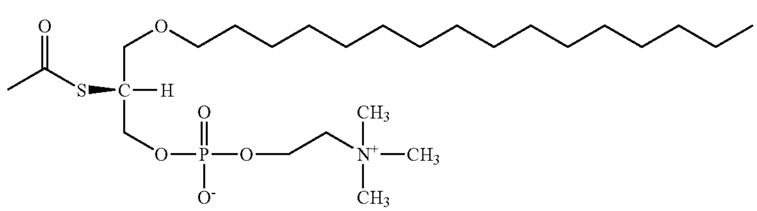 | 2-thio PAF C-16; Cayman 60945 |
| 13 | 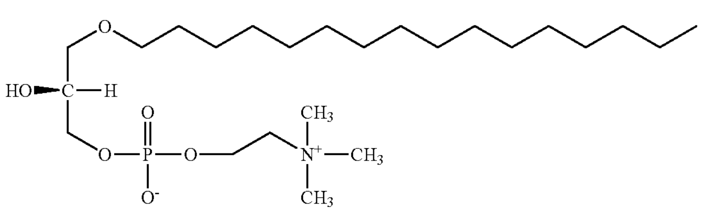 | lyso-PAF C-16 (1-hexadecyl-sn-glycero-3-phosphocholine 3-sn-lysophosphatidylcholine); Sigma L5016, Calbiochem 511077 |

TABLE 1-continued

| | Structure | Name and commercial source |
|---|---|---|
| 14 | 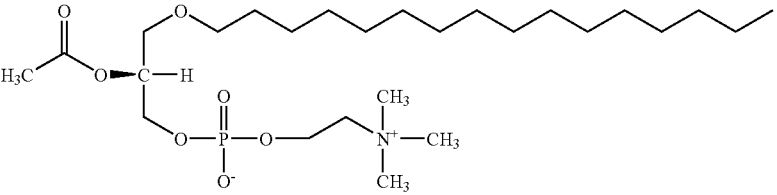 | PAF C-16 (1-hexadecyl-2-acetyl-sn-glycero-3-phosphocholine); Sigma P4904 |
| 15 | 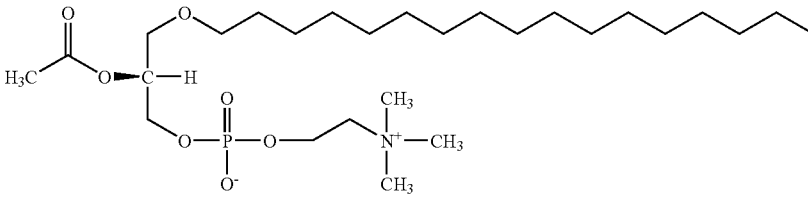 | PAF C-18 (1-O-octadecyl-2-acetyl-sn-glycero-3-phosphocholine); Sigma P6537 |
| 16 | 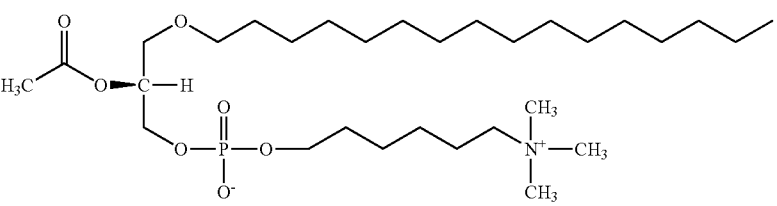 | PAF C-16 antagonist (1-O-hexadecyl-2-acetyl-sn-glycero-3-phospho-(N,N,N-trimethyl)hexanolamine); Calbiochem 511082, Sigma H8771 |
| 17 | 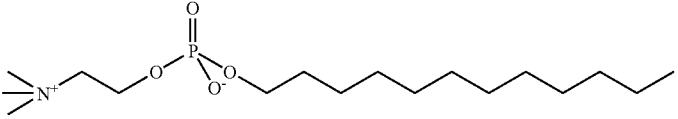 | 12:0 phosphocholine (Dodecylphosphocholine), C12 Miltefosine analog; Avanti 850336 |
| 18 | 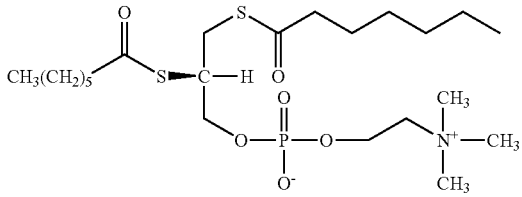 | 1,2-bis(heptanoylthio) glycerophosphocholine; Cayman 62235 |
| 19 | 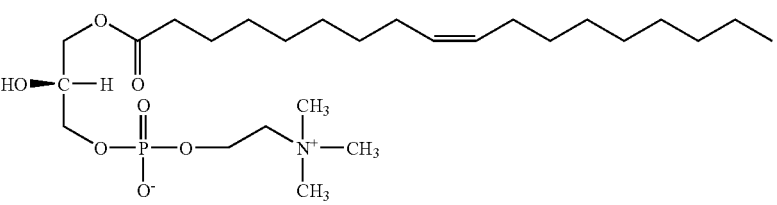 | lysolecithin, oleoyl (1-cis-9-octadecenoyl-sn-glycero-3-phosphocholine); Sigma L1881 |
| 20 | 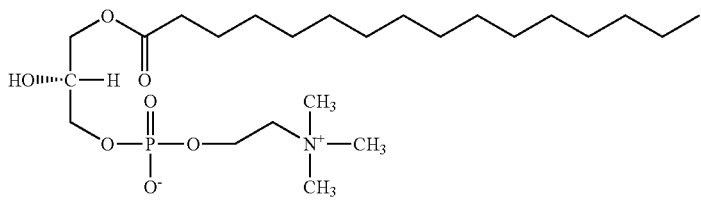 | 16:0 lyso PC or lysolecithin, palmitoyl (1-palmitoyl-2-hydroxy-sn-glycero-3-phosphocholine), C18:1 and C6:0 to C24:0 variants also exist; Avanti 855675, Sigma L5254 |

TABLE 1-continued

| | Structure | Name and commercial source |
|---|---|---|
| 21 | 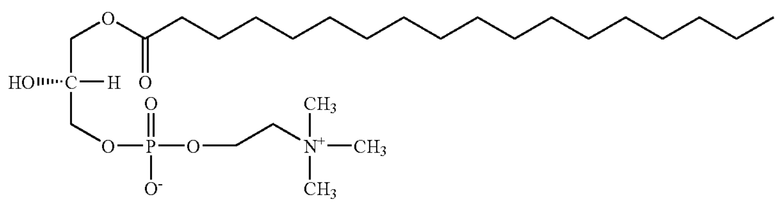 | lysolecithin, stearoyl (1-stearoyl-sn-glycero-3-phosphocholine); Sigma L2131 |
| 23 | 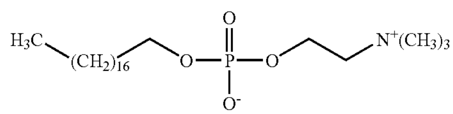 | octadecylphosphocholine (C18:0); Alexis ALX-300-094 |
| 24 | 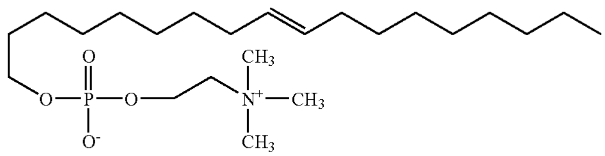 | 1-elaidylphosphocholine (C18:1, trans); Alexis ALX-300-152 |
| 25 | 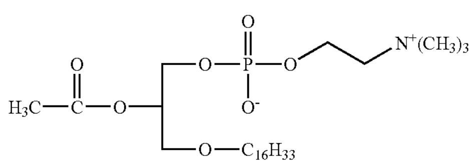 | enantio-PAF C16 (3-O-hexadecyl-2-acetyl-sn-glycero-1-posphocholine); Alexis ALX-301-005 |
| 26 | 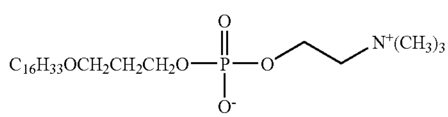 | HPPC (1-O-hexadecyl-propanediol-3-phosphocholine); Alexis ALX-300-091 |
| 27 | 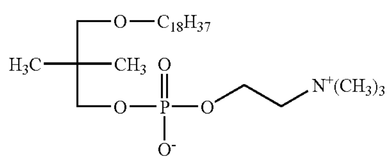 | OPPC (1-O-octadecyl-(2,2-dimethyl)-propanediol-3-phosphocholine); Alexis ALX-300-100 |
| 28 | 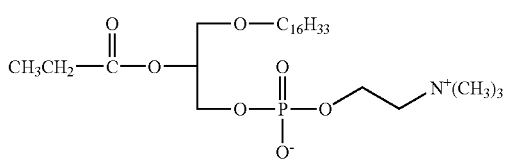 | propionyl-PAF C16 (1-O-hexadecyl-2-propionyl-sn-glycero-3-phosphocholine); Alexis ALX-301-007 |

Among compounds 1 to 21 and 23 to 28, compounds 1, 2, 3, 4, 5 and 6 are a preferred group of compounds. Compounds 9, 17 and 23 to 27 are also preferred. Compounds 1, 2, 3, 4, 5 are an even more preferred group of compounds. Compounds 9, 23 and 24 are also an even more preferred group of compounds. In a particularly preferred embodiment, the compound of formula I is Miltefosine (compound 3).

The compounds to be used in accordance with the present invention are either commercially available as indicated in table 1 or can be prepared by standard methods known in the art.

Compounds of the general formula I belonging to the class of phospholipids (X is O and $R^2$ is a group of formula II), e.g. alkyloxy phospholipids (Y is O) and the corresponding alkylthio derivatives (Y is S), can be prepared as described in the literature (Bittman, R.; *J. Med. Chem.* 1997, 40, 1391-1395; Reddy, K. C.; *Tetrahedron Lett.* 1994, 35, 2679-2682; Guivisdalsky, P. N.; *J. Med. Chem.* 1990, 33, 2614-2621 and references cited therein) or by standard variations of the procedures described therein. Synthesis of the corresponding ester and thioester analogues (Y is OCO and SCO, respectively) can be accomplished by standard acylation of the hydroxy or thio precursor materials.

Compounds of the general formula I belonging to the class of phosphonolipids (X is a direct bond and $R^2$ is a group of formula II), e.g alkyloxy phosphonolipids (Y is O and $R^2$ is a group of formula II) and the corresponding alkylthio derivatives (Y is S) can be prepared as published by Bittman et al. (Bittman, R.; *J. Med. Chem.* 1993, 36, 297-299; Bittman, R.; *J. Med. Chem.* 1994, 37, 425-430 and references cited therein) or by synthetic variations of the procedures described therein. Synthesis of the corresponding ester and thioester analogues (Y is OCO or SCO) can be accomplished by standard acylation of the hydroxy or thio precursor materials.

Introduction of various substituents $R^1$ having a quarternary nitrogen to provide a phosphocholine moiety ($R^1$ is a group of formula IIIa and $n^1$ is 2) or a derivative thereof is widely described in the literature (Reddy, K. C.; *Tetrahedron Lett.* 1994, 35, 2679-2682 and references cited therein) and can be accomplished starting from a suitable glycerol derivative.

In a similar synthetic strategy using an alcohol instead of a glycerol derivative, the corresponding zwitterionic phosphate derivatives ($R^2$ is a $C_{10-20}$ hydrocarbon) can be obtained.

Other substituents $R^1$ employed in the context of this invention, in particular groups having different phosphorus-nitrogen distances ($n^1$ is different from 2) or having nitrogen-containing heterocycles ($R^1$ is a group of formula IIIb or IIIc), can be provided using protocols and strategies outlined in the literature (Eibl, H.; *Chem. Phys. Lipids* 1988, 47, 63-68; Pajouhesh, H.; *J. Lipid Res.* 1984, 25, 294-303; Diembeck, W.; *Chem. Phys. Lipids* 1979, 24, 237-244; Duclos, R.; *J. Med. Chem.* 1994, 37, 4147-4154; Ohno, M.; *Chem. Pharm. Bull.* 1985, 33, 572-582; Krise, J. P.; *J. Med. Chem.* 1999, 42, 3094-3100).

Compounds of the general formula I, wherein $R^2$ is a group of formula IV or V can be obtained by a synthetic combination of the protocols mentioned-above for the introduction of various substituents $R^1$ and $R^2$ and protocols for the syntheses of sphingolipids described in the literature (Merrill, A. H.; *Methods in Enzymology*, Vol. 311, Academic Press, 1999; Koskinen, P. M.; *Synthesis* 1998, 1075; Yamanori, T.; *Chem. Lett.* 1989, 335).

Without being bound by theory, the inner ionic phospholipids, phosphonolipids and phosphate derivatives as described herein may be applied to disrupt rafts and 1) interfere with the transport and aggregation of FcεRI at the cell surface, 2) interfere with the transport and aggregation of rafts by LAT (linker of activation of T cells) at the cell surface. The compounds described herein provide positive results in a cell based assay (degranulation assay) which is an assay for testing substances useful in immunological as well as auto-immunological disorders.

Accordingly, the present invention provides the use of inner ionic phospholipids, phosphonolipids and phosphate derivatives as described herein for the preparation of a pharmaceutical composition for the treatment, prevention and/or amelioration of an immunological disorder related to mast cell sensitization and/or activation, in particular mast cell degranulation.

In the context of the present invention, mast cell sensitization includes binding of IgE to mast cells and/or crosslinking of bound IgE by antigen, which is sometimes referred to as mast cell activation. The present uses and methods are particularly suitable for the treatment, prevention and/or amelioration of an immunological disorder related to mast cell activation.

Disorders to be treated, prevented or ameliorated in the context of the present invention, comprise in particular acute allergic diseases, allergic disorders and/or allergic inflammation. Also autoimmune diseases as well as hyperallergic responses should be treated. In particular, asthma and other immunological diseases may be treated by the use of the compounds as disclosed herein.

Examples of allergic disorders to be treated in the context of the present invention are graft-versus-host disease or transplant rejection.

Graft-versus-host disease in the context of the present invention is a syndrome arising when in particular an allograft, containing immunocompetent cells, mounts an immune response against a host that is unable to reject it because the host is immunologically immature or immunologically compromised or suppressed (e.g. by radiations or drugs). However, the present uses and means are not limited to the amelioration of allograft rejections, but relate in general to an amelioration/medical intervention in transplantations.

The term "transplantation" as employed herein relates preferably to an autologous, an allogenic, a homeogenic, a syngenic or a xenogenic transplantation and also relates to homeotransplants. These transplantations are well known in the art and relate not only to the transplantation of cells, but also to the transplantation of tissues and organs. The transplantation of cells also comprises the transplantation of stem cells. The term "homeotransplantation" as employed herein relates to a graft of tissue obtained from the body of another animal of the same species but with genotype differing from that of the recipient and/or a tissue graft from a donor of one genotype to a host of another genotype, host and donor being members of the same species. Host and donor are called in this respect "allogenic". Also comprised in the term "transplant" are "syngrafts" or "isografts", i.e. transplants from one individual to a genetically identical individual of the same species, e.g., genetically identical twins/siblings. In non-human animals these "syngrafts" may also be carried out on transgenic animals.

Examples of allergic diseases to be treated in the context of the present invention are asthma, allergic rhinitis (hay fever), erythematous lesion, atopic eczema and systemic anaphylaxis, like anaphylactic shock. Urticaria and mastocytosis are among the erythematous lesions to be treated. Specific examples of urticaria include cholinergic urticaria, dermagraphism, cold urticaria, solar urticaria, aquagenic urticaria, drug-related urticaria and toxin-related urticaria.

Accordingly, the present invention and the uses and methods provided herein are particularly useful in the medical intervention of mastocytosis and/or mastocytosis related symptoms as well as in urticaria. Mastocytosis as well as urticaria may be triggered or based on emotional disturbance (for example "blushing"), fever, fatigue, as well as physical stimuli as defined herein above. Accordingly, the substances and compounds provided herein, in particular Edelfosine, Miltefosine, Ilmofosine, 1-O-palmitoyl-2-O-methyl-sn-glycero-3-phosphocholine and 1-O-palmitoyl-2-O-ethyl-sn-glycero-3-phosphocholine, may also be employed in the medical intervention, preventively or in a curative treatment, of exposure to said physical stimuli or exposure to toxins, drugs and/or aggressive substances, such as ethanol, medicaments, like aspirin, opiates, anticholinergics, non-steroidal anti-inflammatory drugs (aspirin), anesthetics, narcotics, antibiotics, bacterial toxins, pesticides, viral, bacterial or fungal infection, mold, venoms, biologic polypeptides (lobster, crayfish, jellyfish), certain foods, food colorings or flavorings, preservatives, perfumes and (radio-)contrast media. Also useful are the herein described compounds, i.e. the inner ionic phospholipids, phosphonolipids and phosphate derivatives, in IgE-mediated disorders, like atopy, antigen sensitization, e.g. pollens, foods, drugs, helminths and the like. Accordingly, the compounds provided herein are particularly useful in the prevention, amelioration and/or treatment of allergies, allergic disorders and allergic reactions.

The inner ionic phospholipids, phosphonolipids and phosphate derivatives described herein may be administered as compounds per se in their use as pharmacophores or pharmaceutical compositions or may be formulated as medicaments. The pharmaceutical compositions may optionally comprise pharmaceutically acceptable excipients, such as carriers, diluents, fillers, desintegrants, lubricating agents, binders, colorants, pigments, stabilizers, preservatives or antioxidants.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, infradermal, intraarterial, rectal, nasal, topical or vaginal administration. Dosage forms for oral administration include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insuflation, for example by a metered inhaler. Dosage forms for topical administration include cremes, gels, ointments, salves, patches and transdermal delivery systems.

Pharmaceutically acceptable salts of compounds that can be used in the present invention can be formed with various organic and inorganic acids and bases. Exemplary acid addition salts comprise acetate, adipate, alginate, ascorbate, benzoate, benzenesulfonate, hydrogensulfate, borate, butyrate, citrate, caphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pectinate, persulfate, 3-phenylsulfonate, phosphate, picate, pivalate, propionate, salicylate, sulfate, sulfonate, tartrate, thiocyanate, toluenesulfonate, such as tosylate, undecanoate and the like. Exemplary base addition salts comprise ammonium salts, alkali metall salts, such as sodium, lithium and potassium salts; earth alkali metall salts, such as calcium and magnesium salts; salts with organic bases (such as organic amines), such as benzazethine, dicyclohexylamine, hydrabine, N-methyl-D-glucamine, N-methyl-D-glucamide, t-butylamine, salts with amino acids, such as arginine, lysine and the like.

Pharmaceutically acceptable solvates of compounds that can be used in the present invention may exist in the form of solvates with water, for example hydrates, or with organic solvents such as methanol, ethanol or acetonitrile, i.e. as a methanolate, ethanolate or acetonitrilate, respectively.

Pharmaceutically acceptable prodrugs of compounds that can be used in the present invention are derivatives which have chemically or metabolically cleavable groups and become, by solvolysis or under physiological conditions, the compounds of the invention which are pharmaceutically active in vivo. Prodrugs of compounds that can be used in the present invention may be formed in a conventional manner with a functional group of the compounds such as with an amino or hydroxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

These pharmaceutical compositions described herein can be administered to the subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should be in the range of 0.1 µg to 5000 mg units per day, in some embodiments 0.1 µg to 1000 mg units per day. If the regimen is a continuous infusion, it may also be in the range of 0.1 ng to 10 µg units per kilogram of body weight per minute, respectively. Progress can be monitored by periodic assessment.

In the context of the present invention, the following modes of topical and systemic administration are preferred.

Topical application of the compounds described herein is envisaged for the relief of indications such as cutaneous mastocytosis, psoriasis, atopic dermatitis, eczema and other dermatoses and mast cell related skin disorders a suitable topical application is in the form of an ointment, cream, gel, foam, solution, lotion, emulsion, spray, liposomal or micellar suspension or other formulation which penetrates the outer layers of the skin. An exemplary suitable concentration of active ingredient in the topically applied formulation described is 0.1% to 2% w/w, such that each 100 gram of ointment, cream, gel, foam, solution, lotion, emulsion, spray, liposomal or micellar suspension or other formulation contains from 0.1 g to 2 g active ingredient. A further suitable concentration of active ingredient in the topically applied formulation is 3% to 6% w/w and a further less preferred but suitable formulation is 7 to 15% w/w. However, it is within the skill of the pertinent artisan that such concentrations be modified. An exemplary suitable dosing regimen for patients undergoing treatment may be determined by the attending physician based upon such factors as the patient's age, sex, weight, and general health. The choice of treatment concentration and dosing regimen will be dependent on the indication. A suitable dosing regimen for the topical formulation envisages treatment of any area of skin preferably 1 to 2 times per day but also suitable is treatment of 3 to 6 times per day. At each application, a thin film should be applied to completely cover the affected area. Treatment duration is between one day and six weeks per treatment cycle.

For the relief of indications such as systemic mastocytosis, histamine-resistant urticaria, allergic rhinitis, asthma, chronic obstructive pulmonary disease (COPD), irritable bowel syndrome and other mast cell related systemic disorders a suitable systemic application is also envisaged and described herein. Such a systemic application may be in the form of fast or slow release formulation, such as capsules, tablets, coated pellets, matrix, liposomes or micelles or other formulation suitable for oral, intranasal, subcutaneous or intramuscular administration. An exemplary suitable concentration of active ingredient in the systemically applied formulation described is 1 mg to 200 mg per tablet, capsule, pellet etc. Furthermore, a suitable dosing regimen for patients undergoing treatment may be determined by the attending physician based upon such factors as the patient's age, sex, weight, and general health. The choice of treatment concentration and dosing regimen will be dependent on the indication. A suitable dose of active ingredient ranges broadly, preferably between about 1 and about 250 microgram per kilogram (µg/kg) of body weight of recipient per treatment. Another suitable dose may be in the range of about 1 to about 100 µg/kg of body weight, and more preferably in the range of about 10 to about 50 µg/kg of body weight. Doses may be administered daily for between one day and six months, or for as long as is deemed necessary and safe, as is readily ascertained by standard tests by the attending physician, depending upon the nature of the disorder being treated. Again, the skilled artisan may modify the protocols provided herein.

The present invention also provides for a method of treatment, amelioration or prevention of disorders or diseases which are related to mast cell sensitization and/or activation. Corresponding diseases/disorders are provided herein above and corresponding useful inner ionic phospholipids, phosphonolipids and phosphate derivatives to be administered to a patient in need of such an amelioration, treatment and/or prevention are also disclosed above and characterized in the appended examples and claims. In a most preferred setting, the compounds described herein are used in these treatment methods by administration of said compounds to a subject in need of such treatment, in particular a human subject.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease; (b) inhibiting the disease, i.e. arresting its development; or (c) relieving the disease, i.e. causing regression of the disease.

A "patient" or "subject" for the purposes of the present invention includes both humans and other animals, particularly mammals, and other organisms. Thus, the methods are applicable to both human therapy and veterinary applications. In the preferred embodiment the patient is a mammal, and in the most preferred embodiment the patient is human.

The present invention is illustrated by the following non-limiting figures and examples.

EXAMPLE 1

Mast Cell Degranulation Assay

Figure 1:
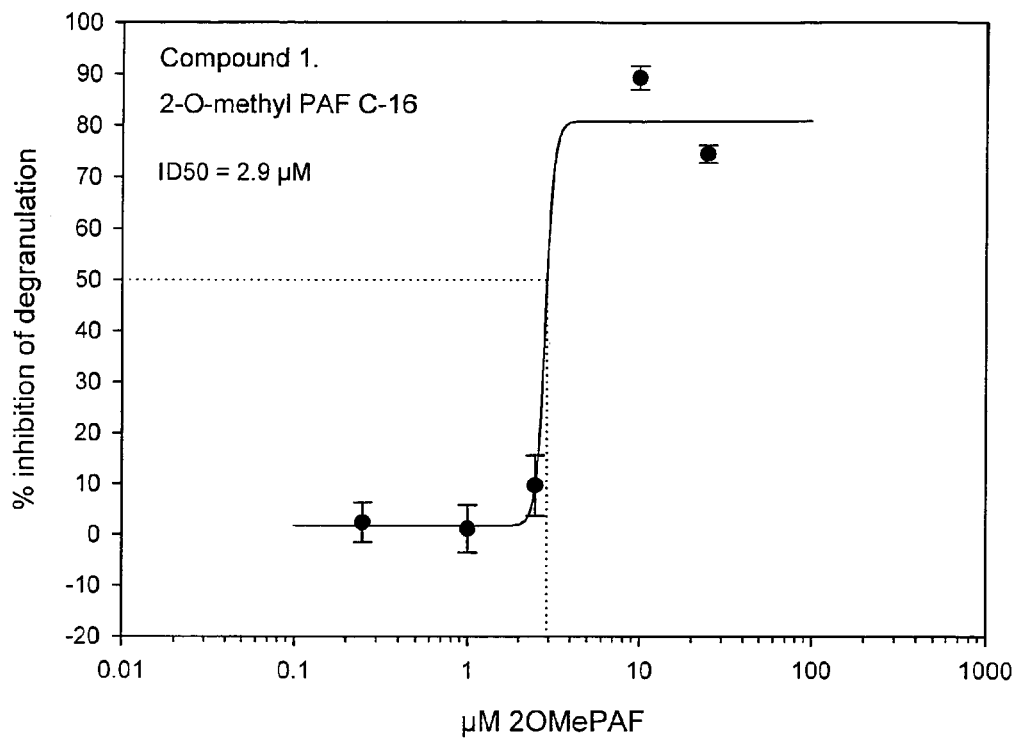
FIGS. 1 to 8 show dose-dependent inhibition of mast cell degranulation by compounds 1 to 6 in comparison to ketotifen fumarate and cromoglycic acid.
Figure 2:
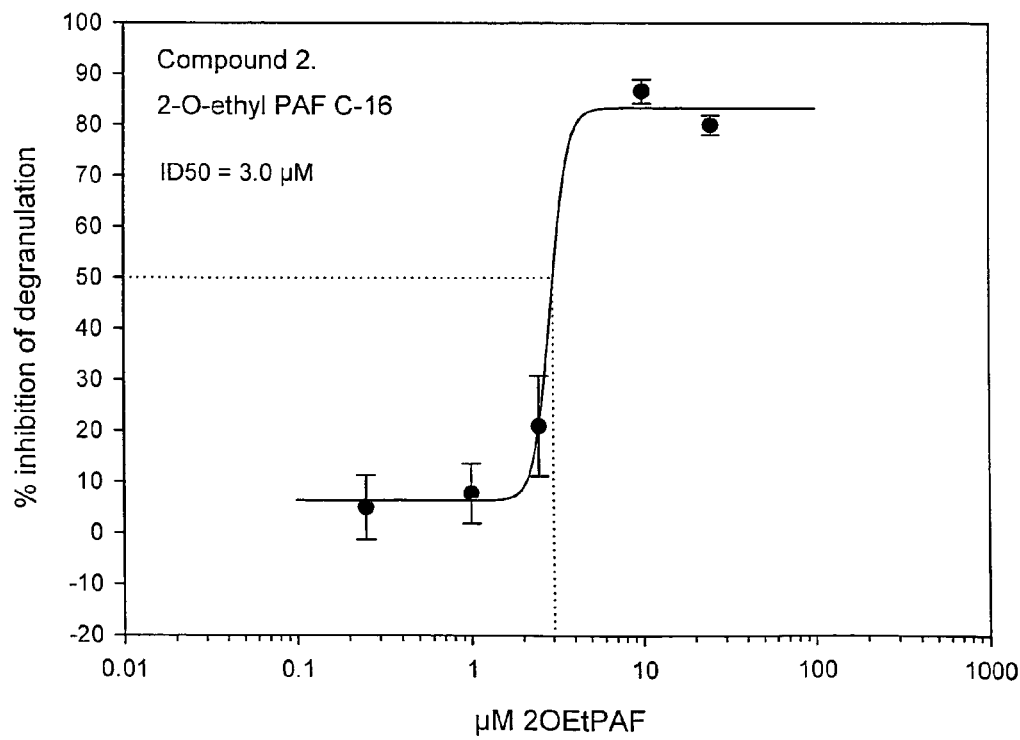
Figure 3:
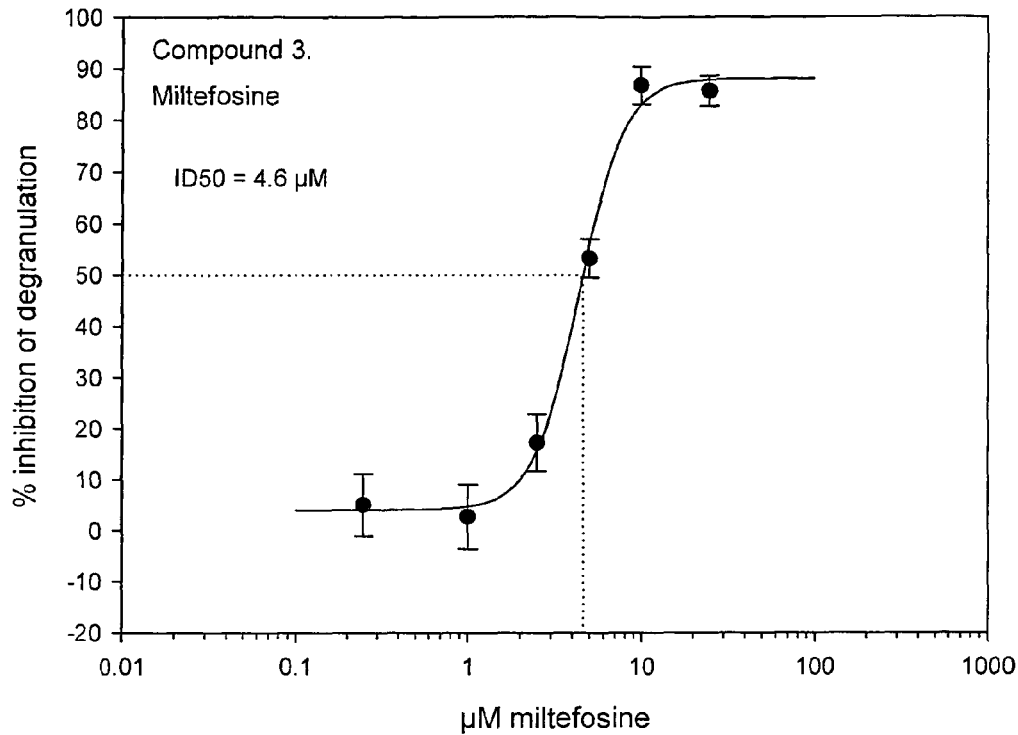
Figure 4:
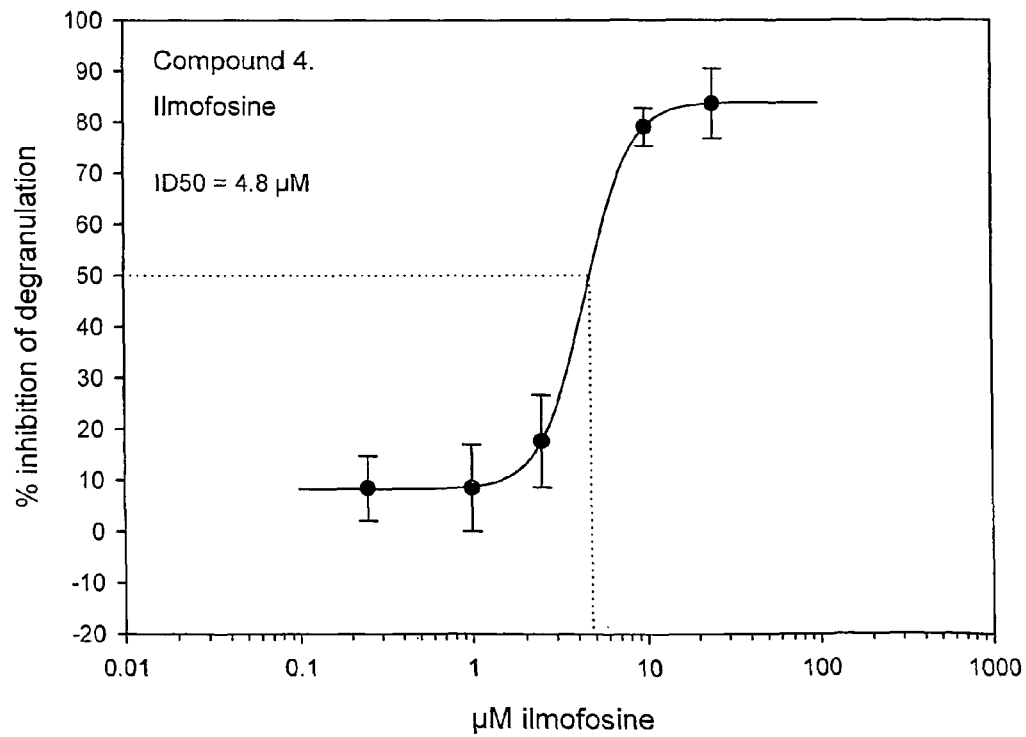
Figure 5:
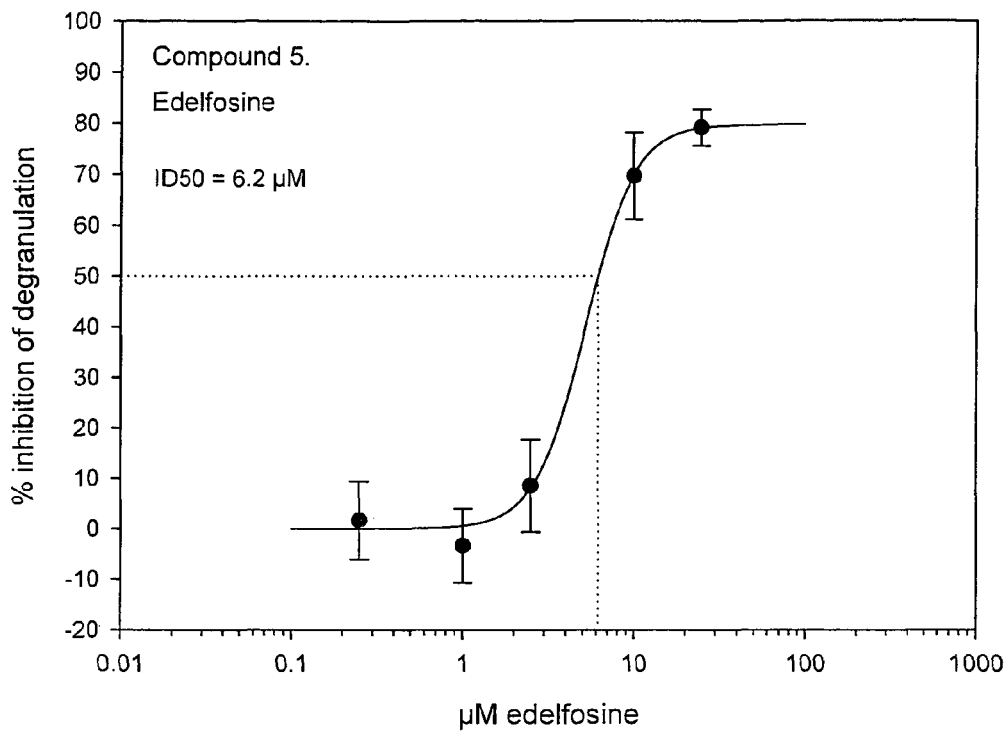
Figure 6:
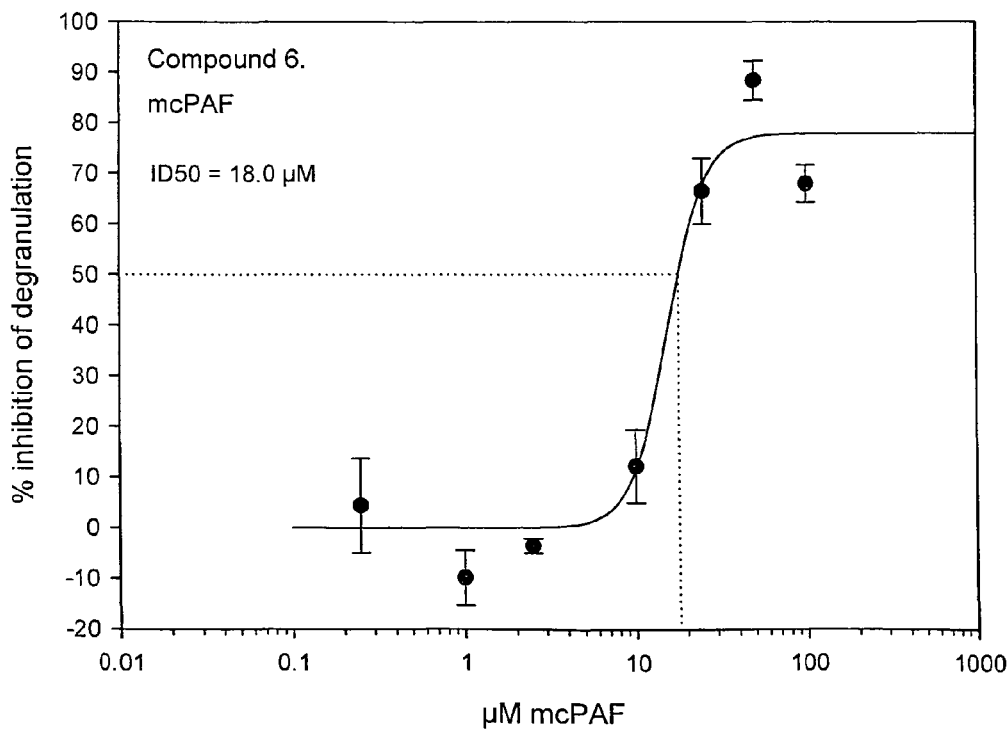
Figure 7:
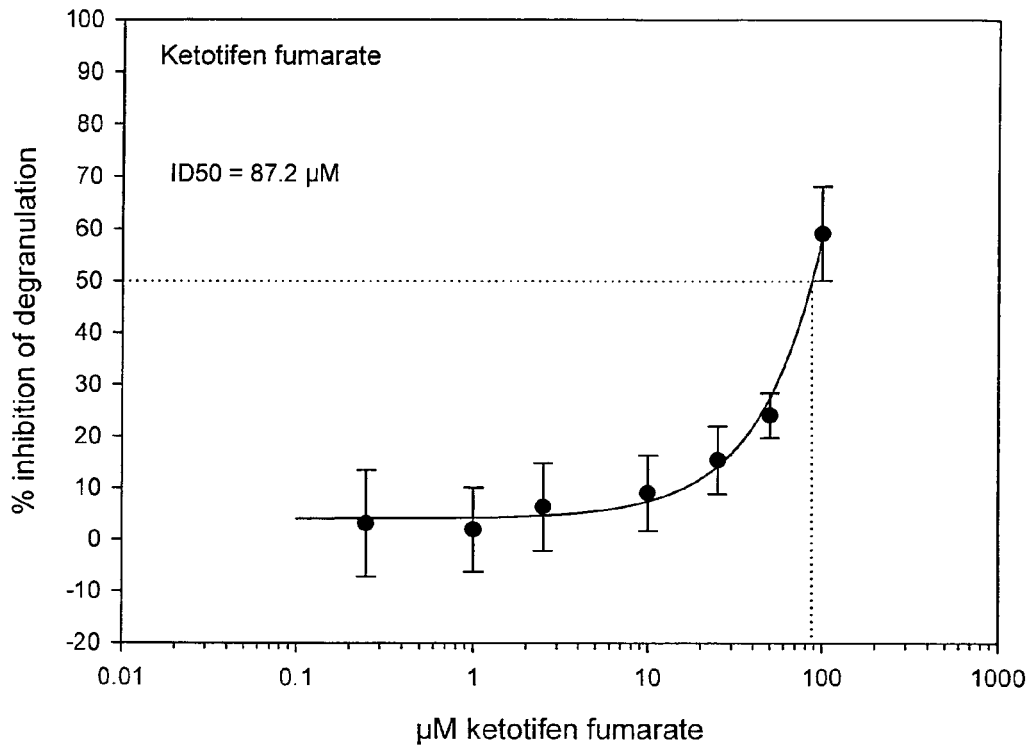
Figure 8:
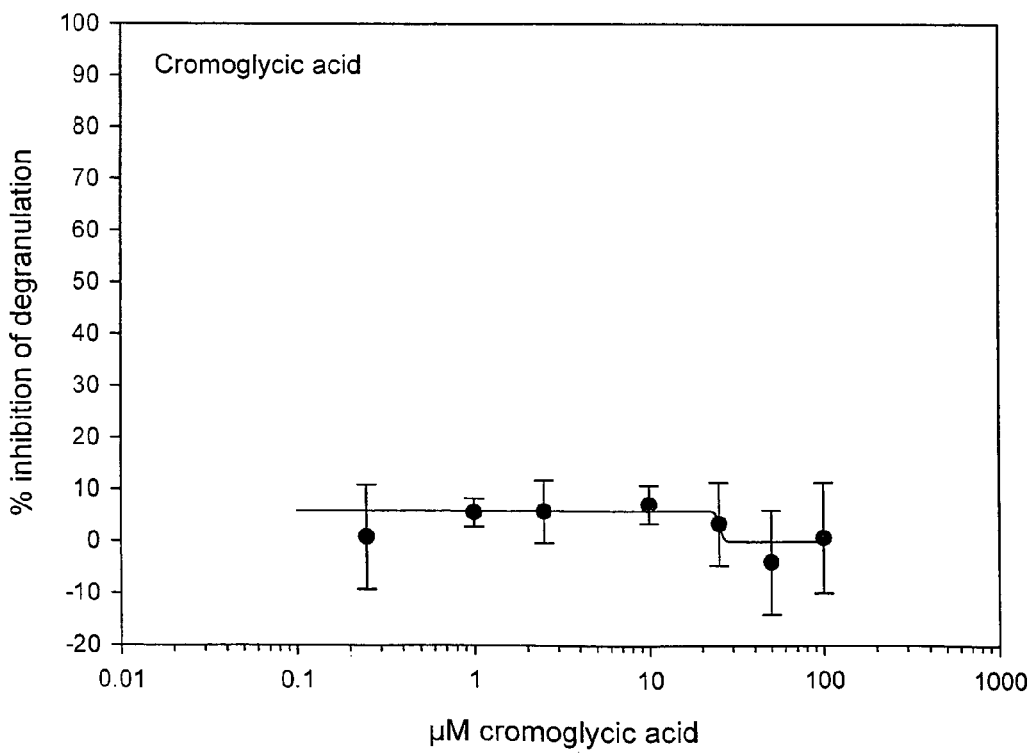

Mast cells are a widely used model system for hyperallergic reactions or asthma. On their surface they express high affinity receptors for IgE (FcεRI). Upon binding of antigen-specific IgE, the receptor cells become sensitive to antigen (allergen). When sensitized cells encounter multivalent antigen the clustering of IgE-FcεRI complexes initiates a cascade of cellular events that ultimately leads to degranulation, that is release of mediators of inflammation and cellular activation, such as cytokines, eicosanoids, histamine and enzymes. Several steps in this cascade are raft-dependent, such as antigen-triggered relocation of FcεRI to rafts, disruption of the signaling complex assembled around LAT and/or dislocation of phosphoinositides, $Ca^{2+}$-influx (raft localization of plasma membrane calcium channels), membrane ruffling (cytoskeletal reorganizations involving Akt/WASP/FAK) and exocytosis. Therefore, the assay can be used as a screening method to identify raft-modulating compounds, in particular compounds useful in the medical management of asthma.

1. Introduction

The assay measures release of β-hexosaminidase as a marker of release of various preformed pharmacological agents in response to clustering of the high affinity IgE receptor (FcεRI) by means of multivalent antigen-IgE complexes. Rat basophilic leukemia (RBL-2H3) cells, a commonly used model of mast cell degranulation, are sensitized with anti-DNP specific IgE and challenged with multivalent DNP-BSA. The release of β-hexosaminidase into the supernatant is measured by enzymatic conversion of the fluorogenic substrate 4-methylumbelliferyl-N-acetyl-β-D-glucosaminide to N-acetyl-β-D-glucosamine and highly fluorescent methylumbelliferone and quantified by fluorescence detection in a Tecan Safire™ plate reader.

2. Materials

Chemicals and Specialty Reagents

Surfact-Amps X-100 solution was obtained from Pierce, DNP-bovine albumin conjugate (DNP-BSA) and 4-methylumbelliferyl-N-acetyl-β-D-glucosaminide (MUG) were from Calbiochem, tri(ethylene glycol) monoethyl ether (TEGME) from Aldrich, DMSO Hybri-Max and human DNP-albumin from Sigma. Rat anti-DNP IgE monoclonal antibody was acquired from Biozol. All cell culture media, buffers and supplements were obtained from Invitrogen except fetal calf serum (FCS) which was from PAA Laboratories (Cölbe, Germany). Other reagents were of standard laboratory quality or better.

Other chemicals are standard laboratory grade or better if not specified otherwise.

Buffers and Solutions

Phosphate buffered saline (PBS) and 1 M HEPES were provided by the in-house service facility. Tyrode's buffer (TyB) consisted of Minimum Essential Medium without Phenol Red (Invitrogen) supplemented with 2 mM GlutaMAX™-I Supplement (Invitrogen) and 10 mM HEPES. Lysis buffer consisted of 25 mM Tris.HCl, pH 7.5, 150 mM NaCl, 5 mM EDTA and 1% (w/v) Triton X-100. Human DNP-BSA was dissolved to 1 mg/ml in Millipore water. MUG substrate solution was 2.5 mM 4-methylumbelliferyl-N-acetyl-β-D-glucosaminide 0.05 M citrate, pH 4.5 and stop solution was 0.1 M $NaHCO_3$/0.1 M $Na_2CO_3$, pH 10.

Cell Culture

RBL-2H3 cells obtained from the German Collection of Microorganisms and Cell Cultures (Braunschweig, Germany) were maintained in 70% Minimum Essential Medium with Earle's Salts/20% RPMI 1640/10% heat-inactivated fetal calf serum) supplemented with 2 mM GlutaMAX™-I in 5% $CO_2$ at 37° C. and routinely checked to be free of mycoplasma contamination. Cells grown in 175 $cm^2$ flasks were split with 0.05% Trypsin/EDTA and resuspended in 20 ml fresh medium. One hundred and 50 µl cell suspension were plated per well into 24 well cluster plates (Costar, Schiphol-Rijk, Netherlands) and cells were used one or two days after plating, respectively.

3. Measurement of β-Hexosaminidase Release

Method

Two to 24 hours before incubation with test compounds the medium was removed and cells were sensitized with 0.4

μg/ml anti-DNP IgE in fresh medium. Following sensitization, cells were washed once with warm TyB and incubated for 60 min with test compound at a maximum of 100 μM or the highest non-toxic concentration (total vehicle concentration adjusted to 1%) or 1% vehicle in TyB at 37° C. DNP-HSA (0.1 μg/ml final concentration) or buffer alone was added and cells incubated for 15 min at 37° C. Plates were centrifuged at 4° C. for 5 min at 250×g and immediately transferred to ice. Supernatants were collected and the cells lysed with lysis buffer. Hexosaminidase activity in supernatants and lysates was measured by incubating 25 μl aliquots with 100 μl MUG substrate solution in a 96-well plate at 37° C. for 30 min. The reaction was terminated by addition of 150 μl stop solution. Fluorescence was measured in a Tecan Safire™ plate reader at 365 nm excitation and 440 nm emission settings.

Quantification of Assay Results

Each compound is tested in duplicates in at least three independent experiments. β-hexosaminidase release is calculated after subtraction of unspecific release (release without addition of antigen) using the formula:

% degranulation=100×$RFU$ supernatant/$RFU$ lysate

Inhibition of β-hexosaminidase release with respect to control is calculated as follows:

% inhibition=100×(1−($RFU$ supernatant of compound/$RFU$ supernatant of control))

Values for inhibition of degranulation from independent experiments are averaged and accepted when the standard deviation (SD)≦15%.

Table 2 shows the results obtained in the mast cell degranulation assay.

TABLE 2

Inhibition of mast cell degranulation

| | structure | Name and commercial source | ID50 (µM) | maximum inhibition (concentration used) | CD50 (µM) |
|---|---|---|---|---|---|
| 1 | 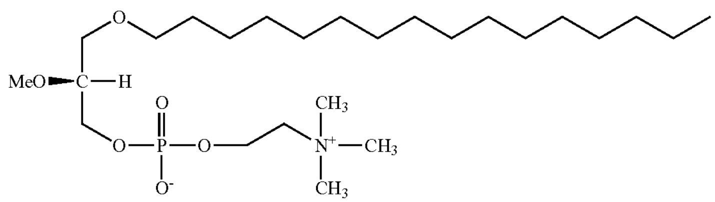 | 2-O-methyl PAF C-16; Cayman 60902 | 2.9 | 89% (10 µM) | 48.2 |
| 2 | 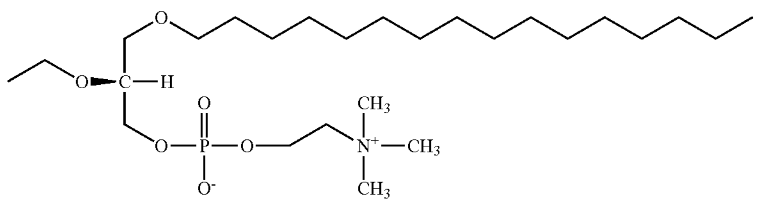 | 2-O-ethyl PAF C-16; Cayman 60925 | 3.0 | 86% (10 µM) | 57.2 |
| 3 | 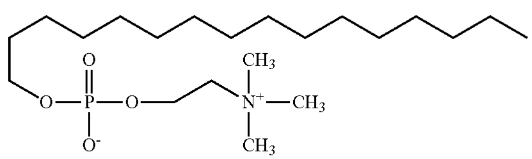 | Miltefosine (1-hexadecylphosphoryl-choline, HePC; Calbiochem 475841 | 4.6 | 87% (10 µM) | 69.5 |
| 4 | 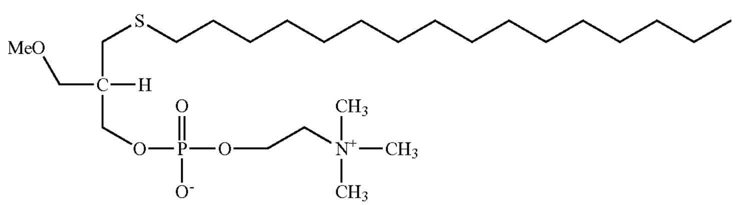 | Ilmofosine (1-hexadecylmercapto-2-methoxymethyl-3-propyl phosphoric acid monocholine ester); Sigma I2409 | 4.8 | 84% (25 µM) | n.d. |

TABLE 2-continued

Inhibition of mast cell degranulation

| | structure | Name and commercial source | ID50 (μM) | maximum inhibition (concentration used) | CD50 (μM) |
|---|---|---|---|---|---|
| 5 | 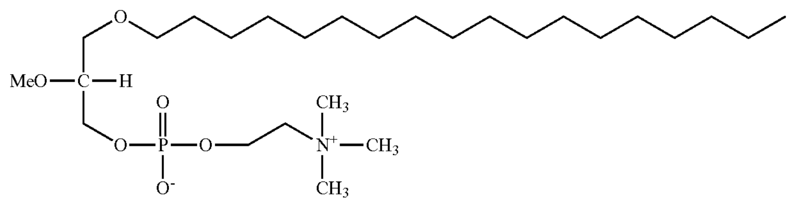 | Edelfosine (18:0-1:0 Diether PC); Calbiochem 341207, Sigma E1779 | 6.2 | 79% (25 μM) | 59.0 |
| 6 | 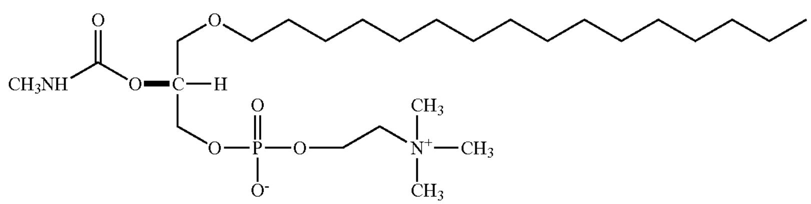 | mcPAF C-16 (1-O-palmitoyl-2-(N-methylcarbamyl)-sn-glycero-3-phosphocholine); Sigma H4648 | 18.0 | 88% (50 μM) | >100 |
| 7 | 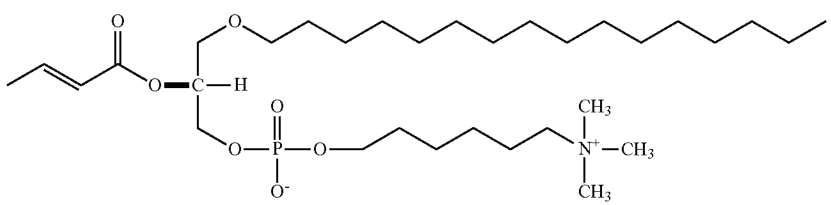 | butenoyl PAF C-16; Cayman 60929 | 11.0 | 69% (25 μM) | 79.6 |
| 8 | 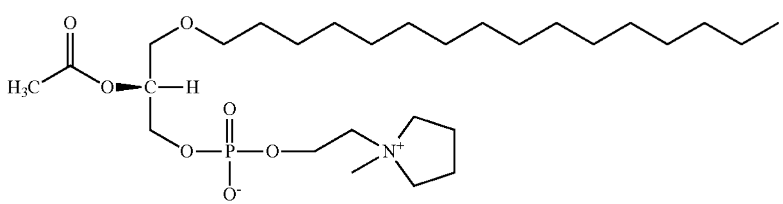 | pyrrolidino PAF C-16; Cayman 60909 | 13.7 | 53% (25 μM) | 50.2 |
| 9 | 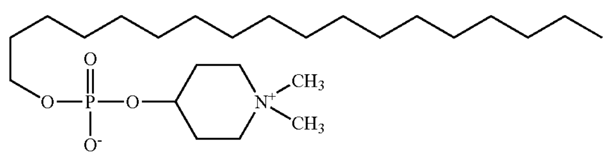 | perifosine (octadecyl-(N,N-dimethyl-piperidinio-4-yl)-phosphate); Asta Medica D-21266 | 2.8 | 85% (10 μM) | 76.7 |

TABLE 2-continued

Inhibition of mast cell degranulation

| | structure | Name and commercial source | ID50 (µM) | maximum inhibition (concentration used) | CD50 (µM) |
|---|---|---|---|---|---|
| 10 | 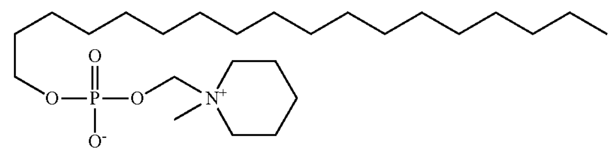 | octadecyl-(2-(N-methyl-piperidinio)-ethyl)-phosphate; Asta Medica D-20133 | n.d. | n.d. | n.d. |
| 11 | 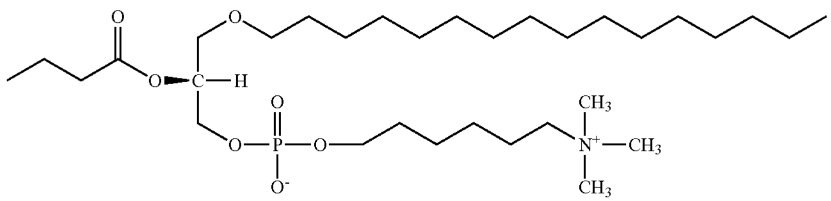 | butanoyl PAF C-16; Cayman 60928 | n.d. | 48% (25 µM) | 68.4 |
| 12 | 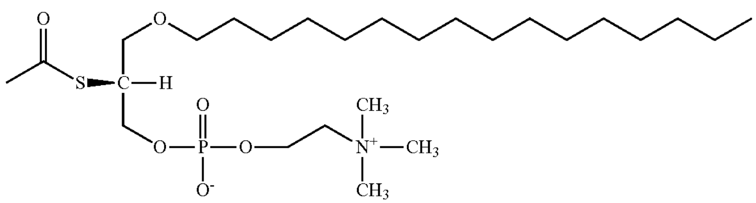 | 2-thio PAF C-16; Cayman 60945 | n.d. | 41% (25 µM) | 86.5 |
| 13 | 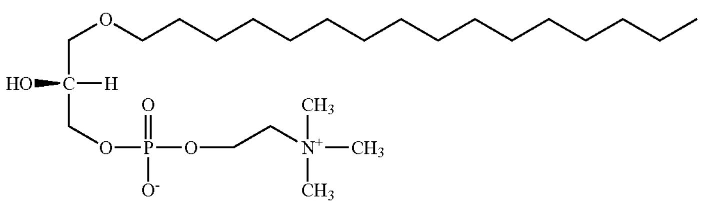 | lyso-PAF C-16 (1-hexadecyl-sn-glycero-3-phosphocholine 3-sn-lysophosphatidylcholine); Sigma L5016, Calbiochem 511077 | n.d. | 41% (25 µM) | 58.8 |
| 14 | 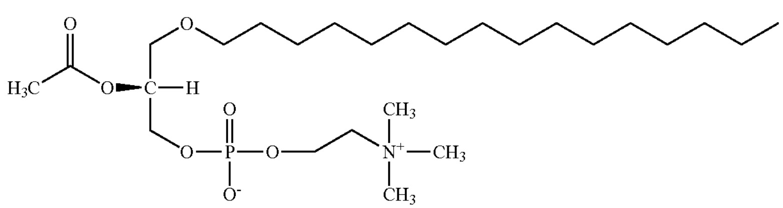 | PAF C-16 (1-hexadecyl-2-acetyl-sn-glycero-3-phosphocholine); Sigma P4904 | n.d. | 42% (25 µM) | 57.7 |

TABLE 2-continued

Inhibition of mast cell degranulation

| | structure | Name and commercial source | ID50 (μM) | maximum inhibition (concentration used) | CD50 (μM) |
|---|---|---|---|---|---|
| 15 | 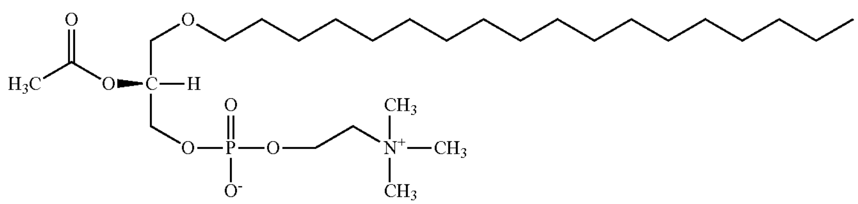 | PAF C-18 (1-O-octadecyl-2-acetyl-sn-glycero-3-phosphocholine); Sigma P6537 | n.d. | n.d. | n.d. |
| 16 | 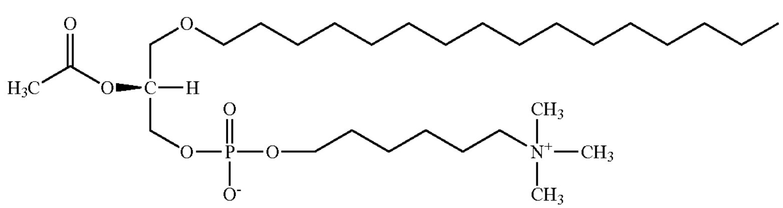 | PAF C-16 antagonist (1-O-hexadecyl-2-acetyl-sn-glycero-3-phospho-(N,N,N-trimethyl)hexanolamine); Calbiochem 511082, Sigma H8771 | n.d. | 45% (25 μM) | 51.3 |
| 17 | 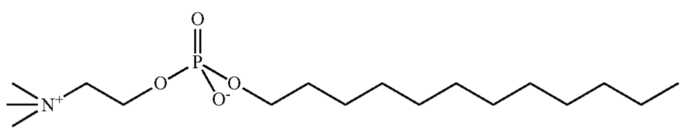 | 12:0 phosphocholine (Dodecylphosphocholine), C12 Miltefosine analog; Avanti 850336 | 7.1 | 76% (25 μM) | >100 |
| 18 | 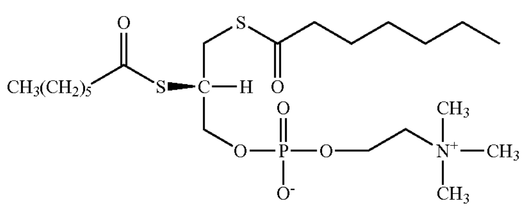 | 1,2-bis(heptanoylthio) glycerophosphocholine; Cayman 62235 | n.d. | n.d. | n.d. |
| 19 | 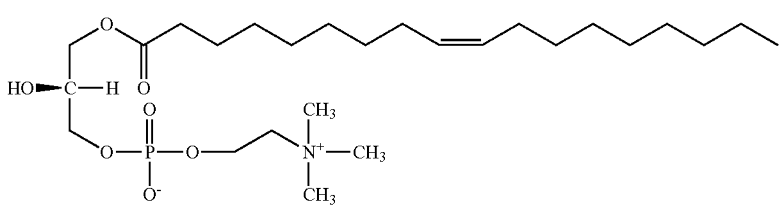 | lysolecithin, oleoyl (1-cis-9-octadecenoyl-sn-glycero-3-phosphocholine); Sigma L1881 | n.d. | n.d. | n.d. |

TABLE 2-continued

Inhibition of mast cell degranulation

| | structure | Name and commercial source | ID50 (μM) | maximum inhibition (concentration used) | CD50 (μM) |
|---|---|---|---|---|---|
| 20 | 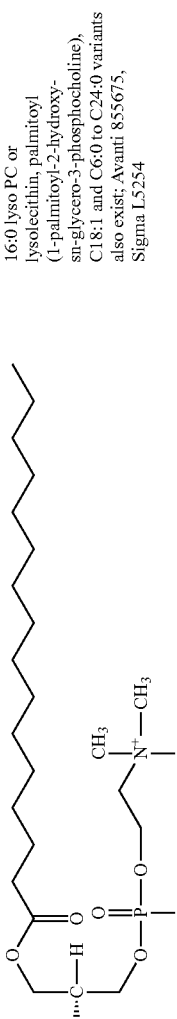 | 16:0 lyso PC or lysolecithin, palmitoyl (1-palmitoyl-2-hydroxy-sn-glycero-3-phosphocholine), C18:1 and C6:0 to C24:0 variants also exist; Avanti 855675, Sigma L5254 | n.d. | 26% (25 μM) | 70.3 |
| 21 | 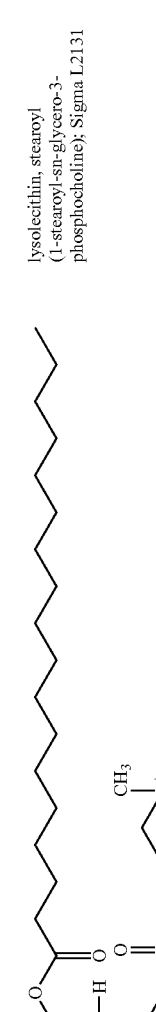 | lysolecithin, stearoyl (1-stearoyl-sn-glycero-3-phosphocholine); Sigma L2131 | n.d. | n.d. | n.d. |
| 22 | 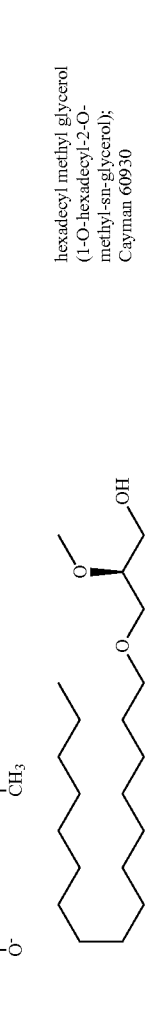 | hexadecyl methyl glycerol (1-O-hexadecyl-2-O-methyl-sn-glycerol); Cayman 60930 | n.d. | 15% (100 μM) | >100 |
| 23 | 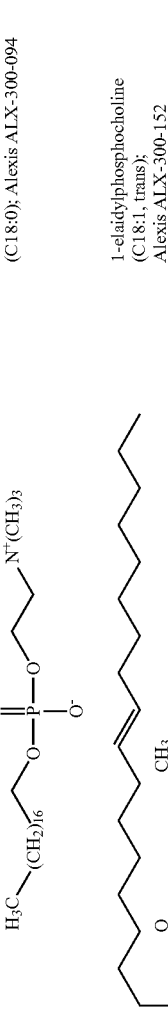 | octadecylphosphocholine (C18:0); Alexis ALX-300-094 | 2.6 | 82% (10 μM) | >50 |
| 24 | 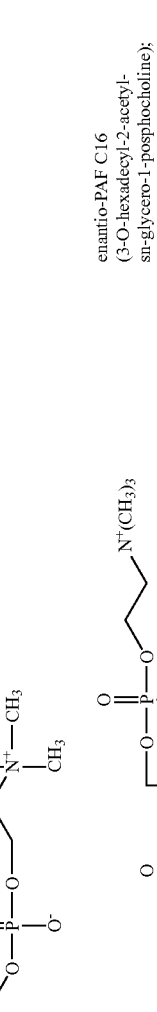 | 1-elaidylphosphocholine (C18:1, trans); Alexis ALX-300-152 | 2.9 | 92% (10 μM) | 59.6 |
| 25 | 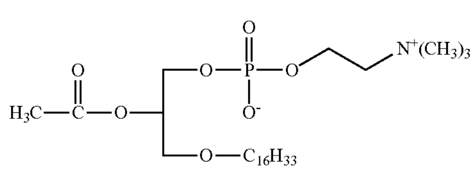 | enantio-PAF C16 (3-O-hexadecyl-2-acetyl-sn-glycero-1-posphocholine); Alexis ALX-301-005 | 3.0 | 82% (10 μM) | n.d. |

TABLE 2-continued

Inhibition of mast cell degranulation

| | structure | Name and commercial source | ID50 (µM) | maximum inhibition (concentration used) | CD50 (µM) |
|---|---|---|---|---|---|
| 26 | $C_{16}H_{33}OCH_2CH_2CH_2O-\overset{O}{\underset{O^-}{P}}-O-CH_2CH_2-N^+(CH_3)_3$ | HPPC (1-O-hexadecyl-propanediol-3-phosphocholine); Alexis ALX-300-091 | 3.1 | 90% (10 µM) | n.d. |
| 27 | OPPC structure with $O-C_{18}H_{37}$, $CH_3$ groups | OPPC (1-O-octadecyl-(2,2-dimethyl)-propanediol-3-phosphocholine); Alexis ALX-300-100 | 8.0 | 85% (25 µM) | n.d. |
| 28 | propionyl-PAF C16 structure with $O-C_{16}H_{33}$, $CH_3CH_2-C(O)-O-$ | propionyl-PAF C16 (1-O-hexadecyl-2-propionyl-sn-glycero-3-phosphocholine); Alexis ALX-301-007 | 13.1 | 64% (25 µM) | n.d. |

ID50, concentration at which 50% of maximal inhibition is reached.

CD50, concentration at which 50% of maximal lactate dehydrogenase release is reached in a cytotoxicity test (Promega Cytotox-One cat. #67891).

n.d. not done

Table 2 lists potency (ID50) and maximum inhibition in the mast cell degranulation activity as well as cytotoxicity (CD50) in a membrane integrity assay (Promega Cytotox-One, cat. #67891) of the compounds 1 to 28. An inhibition of degranulation of 50% or greater combined with a therapeutic index (CD50/ID50) of 10 or greater was considered to be relevant for development of pharmaceutical derivatives. Thus the closely related compounds 1 and 2 (2-O-methyl PAF C-16 and 2-O-ethyl PAF C-16) and compounds 9, 23 and 24 have similar potencies and maximum inhibitory activities, but compound 9 is less cytotoxic. Compounds 3, 4 and 5 (Miltefosine, Ilmofosine and Edelfosine) and compounds 17, 25, 26 and 27 have similar maximum activities but lower potencies and in the case of Edelfosine, a higher cytotoxicity. Compounds 6, 7, 8 (mcPAF C-16, butenoyl PAF C-16 and pyrrolidino PAF C-16) and 28 are only 15 to 40% as potent as compounds 1, 2, 9, 23 and 24. Compounds 6 and 9 have low toxicity and hence have a potential therapeutic index of greater than 10. None of the remaining compounds achieved greater than 50% inhibition at the maximum tested doses.

Compounds 1 to 5, 9, 17 and 23 to 27 showed an inhibition of above 75% at 10 or 25 µM and are thus particularly preferred in the context of the present invention. Compound 6 showed an inhibition of above 75% at 50 µM and is thus also preferred in the context of the present invention. Compounds 7, 8, 11 to 14, 16, 20 and 28, even though not as active as compounds 1 to 6, 9, 17 and 23 to 27, still showed activity in the mast cell degranulation assay and can thus suitably be employed in the context of the present invention. Compound 22 was tested for comparative purposes and gave poor results in the mast cell degranulation assay.

The results for exemplary compounds are further illustrated in FIGS. 1 to 8 which show the activity of compounds in inhibition of mast cell degranulation. The assay is an industry standard for determination of mast cell stabilizing activity of potential antiallergic compounds. It can be seen that whereas two approved and clinically used mast cell stabilizers (ketotifen fumarate and cromogylcic acid) have no or only low activity in this assay (FIGS. 7 and 8), the compounds 1 to 6 demonstrate good potency (ID50) at low micromolar concentrations (FIGS. 1 to 6).

EXAMPLE 2

Inhibition of Activation and Mediator Release of Human Skin Mast Cells In Vitro and In Vivo Experimental Design In Vitro and Ex Vivo-experiments:

To determine whether Miltefosine can inhibit the activation and mediator release of human skin mast cells in vitro, we used the following techniques and materials and experimental approaches:

Preparation of Stock Solution of Miltefosine

Stock solution of Miltefosine (5 mM) was prepared in DMSO and stored at −20° C. For preparation of the working concentration (2 mM), the stock solution was diluted with PAG-CM (PAG-CM=PIPES Albumin Glucose with Calcium und Magnesium). All other dilutions of Miltefosine were prepared with 40% DMSO in PAG-CM buffer.

Isolation and Purification of Human Basophils

Human basophils were isolated from whole blood using ficoll paque (D=1.077). Briefly, heparinized whole blood was diluted 1:3 with PBS (w/o Ca and Mg), layered on the ficoll paque solution, and centrifuged for 30 min at 400×g. Low-density particles such as lymphocytes, monocytes, basophils, and platelets were recovered from the interface between the plasma and ficoll solution. The cell suspension from the interface was centrifuged twice at 200×g for 10 min for removal of thrombocytes from the basophil fraction. The number of basophils in the cell suspension was determined by Toluidin blue staining. The yield of basophils was approximately 2%. These pre-purified basophils were used for the histamine release assay. For the cytokine release assays, basophils were further purified using the "Basophil Isolation Kit" for depletion of non-basophils from the interface cell suspension. To this end, the cell suspension was incubated in a first step with hapten-conjugated antibody mix containing CD3, CD7, CD14, CD5, CD16, CD36 und CD45RA for 30 min followed by exposure to magnetic beads coated with hapten-specific antibodies. Cells bound to the magnetic beads were separated with AutoMACS. The negative fraction of this separation protocol contained basophils with a purity of more than 95 percent.

Isolation and Purification of Primary Cutaneous Mast Cells

Tissue mast cells were isolated from human skin obtained during cosmetic surgery. Use of human skin was conducted according to the Declaration of Helsinki Principles and was approved by the Institutional Review Board of the Charité-Universitätsmedizin Berlin. For isolation of mast cells, the epidermis was enzymatically detached by an overnight incubation at 4° C. with dispase at a concentration of 1 mg/ml. The remaining dermis was dispersed by incubation with a mix of collagenase I and hyaluronidase for 1 h at 37° C. Dispersion was repeated three times, and the collected cells were washed. Thereafter, cells were cultured overnight at 37° C. and 5% Co2/95% air in basal Iscove Medium supplemented with 10% fetal calf serum, glutamin, penicillin, streptomycin, and monothioglycerol. The separation of the nonadherent mast cells from the adherent cells was achieved through repeated washing with cold PBS. For the histamine release assay, collected cells were suspended in PAG-CM and affinity purified using CD117 micro beads (Miltenyi Biotech) directed against the Kit receptor (CD 117). Briefly, dermal cells were incubated for 30 min at 4° C. with CD117 magnetic beads. Separation of labeled from unlabeled cells was achieved by passing cells over the AutoMACS System. The final mast cell purity was >90% as measured by Toluidin blue staining. The viability of mast cells was >95% as assessed by Trypan blue staining (Grützkau et al 2000, Artuc et al 2002).

Histamine Release Assay (HRA)

The quantification of histamine levels was achieved using an automated histamine-analyser system (Firm Borgwelt Technik). The wavelength of the excitation was 355-360 nm and the emission wavelength of fluorescence measurement was 450-460 nm. The intensity of fluorescence was directly proportional to the concentration of histamine in the samples. The amount of released histamine was calculated according to the following formula: net histamine release=(release−blank)×(100/complete). "Release", in this context, was defined as the supernatant of stimulated cells, e.g. by anti-IgE, whereas supernatants of non stimulated cells, i.e. spontaneous release, was termed "blank". "Complete" stands for the total histamine content of mast cells (after lysing with perchloric acid). The histamine release assays were performed in the PAG-CM buffer system. The numbers of mast cells or basophils in each sample used for histamine release assays was approximately $1 \times 10^4$ cells. For stimulation, cells were exposed to anti-IgE, Substance P, Ca-ionophore, or C5a.

Pre-incubation with Miltefosine and Stimulation of Cells

Cells were washed twice with PBS w/o Ca, Mg, once with PAG-CM and afterwards centrifuged for 10 min at 250×g. The cell pellets were suspended in pre-warmed PAG-CM (37° C.). The cell suspension was distributed into 18 falcon tubes for 6 different treatments and 3 incubation periods (10 min, 30 min, or 60 min) each:

1-PAG-CM,
2-DMSO/PAG-CM,
3-5 µM Miltefosine,
4-10 µM Miltefosine,
5-20 µM Miltefosine,
6-25 µM Miltefosine.

Incubations were performed in a warm water bath (37° C.).

Aliquots of the pre-incubated cell suspensions were added to prepared tubes and incubated for 30 minutes at 37° C. for stimulation:

tube 1=2% perchloric acid,
tube 2=PAG*CM,
tube 3=anti-IgE or Substance P or Ca-Ionophore.

Reactions were stopped with cold PAG-CM buffer and samples were centrifuged for 10 min at 4° C. and 250×g. Supernatants were decanted into special cups for histamine estimation. For determination of cytokines or arachidonic acid metabolites, cell suspensions were divided after pre-incubation with different concentrations of Miltefosine into two aliquots and incubated for 30 minutes with or without anti-IgE (at 37° C.), followed by centrifugation for 10 min at 250×g. Supernatants were stored at −80° C. for later analysis of arachidonic acid metabolites. The cell fraction was resuspended in basal Iscove Medium supplemented with 10% fetal calf serum, glutamine, penicillin, streptomycin, and monothioglycerol and cultured for the next 24 hours at 37° C. Afterwards, the supernatants were removed and stored at −80° C. (for analysis of TNF alpha).

In Vivo-experiments:

To provide proof of concept that Miltefosine inhibits IgE-dependent human mast cell stimulation and mediator release in vivo we performed a study on selected allergic volunteers with known type-I-sensitizations (n=5). The volunteers were subjected to standard prick testing with their known allergens on both forearms as well as with positive (histamine) and negative (saline) controls (Table 3). Using a double blind, placebo controlled approach, one forearm of each test person was pre-treated with topical Miltefosine (6% solution). The contralateral side was subjected to a pre-treatment with a placebo solution (saline), both two hours prior to the prick test. Subsequently, developing skin symptoms were measured with high-quality standardized methods, i.e. macroscopic standard prick test-evaluation (Heinzerling et al 2005), volumetric imaging, thermography, and digital time lapse photography (DTLP). Volunteers known to suffer from permanent severe diseases, especially those affecting the immune system, were excluded from the study. None of the volunteers took any oral histamines or leukotriene antagonists within 7 days prior to the beginning of the study. Moreover, none of them took any oral or depot corticosteroids or other immunosuppressive drugs within 21 days before the testing.

The course of developing lesions (wheal and erythema size) was assessed macroscopically by measuring vertical and perpendicular diameter of wheal and erythema size. Subsequently, the sum of both diameters was divided by two. In addition, volumetric and thermographic imaging as well as DTLP was performed before and at defined time points after prick testing.

Thermographic imaging detects radiation in the infrared range of the electromagnetic spectrum with a special thermographic camera. Infrared radiation is emitted by all objects based on their temperature. The amount of radiation emitted by an object increases with temperature. Therefore, thermography allows for the detection of variations in temperature. As the development and regression of prick test lesions is accompanied with temperature changes and thermographic imaging is able to discriminate even small temperature changes (at 0.1° C.), thermography is a highly accurate method to visualize prick test reactions. Thermographic imaging was performed in intervals of five minutes for a time period of one hour following prick testing (FLIR ThermaCAM S60, FLIR Systems GmbH, Frankfurt/Main, Germany).

Digital time lapse photography (DTLP) was performed to monitor macroscopically detectable prick test lesions. Digital photos were taken in intervals of 5 minutes for a time period of one hour and the skin area affected by prick test reactions is calculated using a planimetric analysis system.

Volumetric analyses of prick test lesions were performed using a novel volumetric system (Primos contact, GFM Messtechnik GmbH, Teltow, Germany). This system measures the tumescence of prick test lesions in relation to the skin surface. Volumetry was performed in intervals of 5 minutes during the period of thermographic and digital photographic imaging.

TABLE 3

Overview of the allergic volunteers

| Volunteer No. | Sex | Age | Allergen | Miltefosine pre-treatment | Placebo (NaCl) pre-treatment |
|---|---|---|---|---|---|
| 1 | m | 55 | grass mix | right arm | left arm |
| 2 | m | 30 | grass mix | left arm | right arm |
| 3 | m | 40 | derm. pteroniss. | right arm | left arm |
| 4 | f | 26 | cat hair | right arm | left arm |
| 5 | f | 33 | derm. pteron. | right arm | left arm |

Results

In Vitro and Ex Vivo-experiments:

Effect of Miltefosine on Histamine Release in C57 Cells

Figure 9:
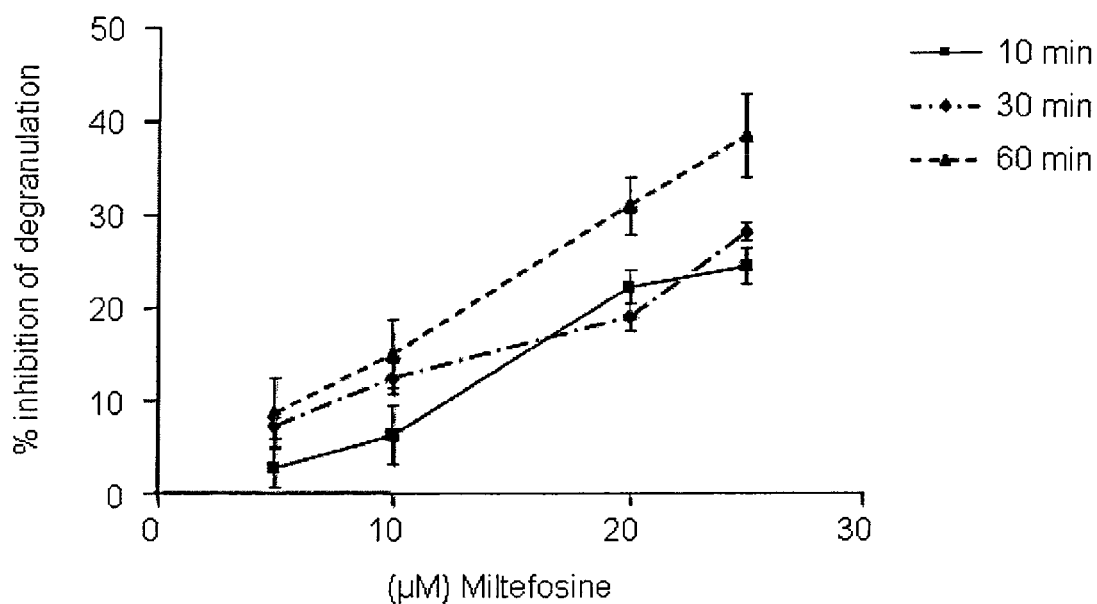
FIGS. 9 and 10 show the inhibitory effect of Miltefosine on the histamine release induced in C57 cells by anti-human-IgE and by the ionophore A23187, respectively.

The C57 mouse mast cell line transfected with the alpha chain of the human high affinity IgE receptor showed a reliable degranulation response after stimulation with anti-human-IgE. Pre-incubation of C57 cells with various concentrations of Miltefosine resulted in an inhibition of histamine release. This inhibition was dose- and time-dependent (FIG. 9). The maximal inhibition (40 percent) was achieved after 60 min pre-incubation with Miltefosine. Miltefosine inhibited not only IgE receptor dependent histamine release, but also Ca-ionophore induced histamine release in C57 cells (FIG. 10).

Figure 10:
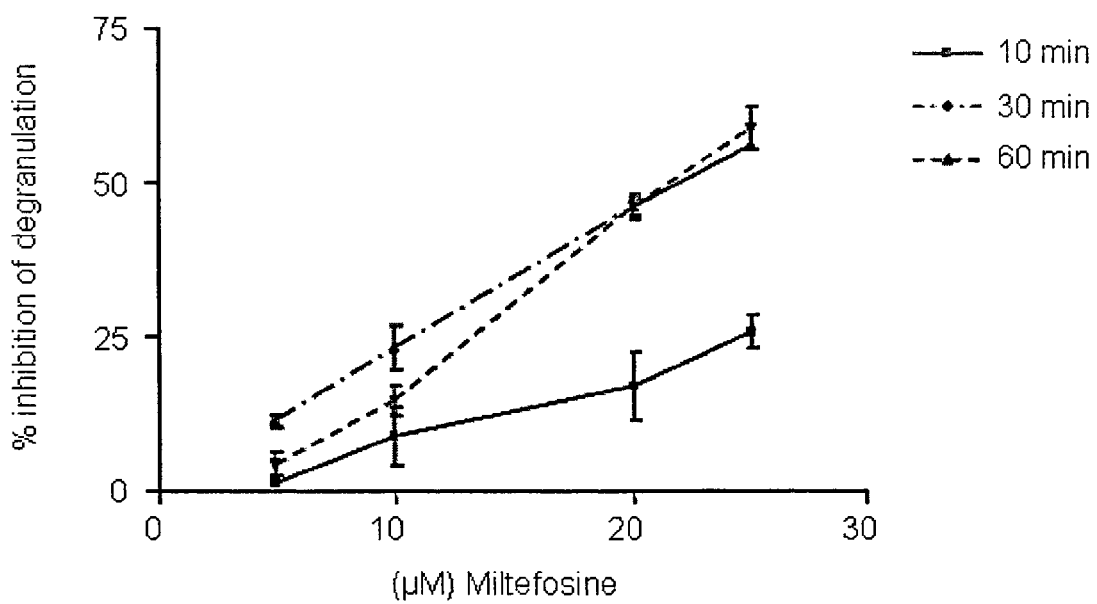

Miltefosine inhibited Ca-ionophore induced histamine release dose-dependently with 25 μM representing the maximal inhibitory concentration tested (FIG. 10). Various pre-incubation times resulted in significantly different inhibitory effects on anti-IgE dependent or Ca-ionophore-induced histamine release (FIGS. 9 and 10).

Effects of Miltefosine on Histamine Release in Human Mast Cells

Figure 11:
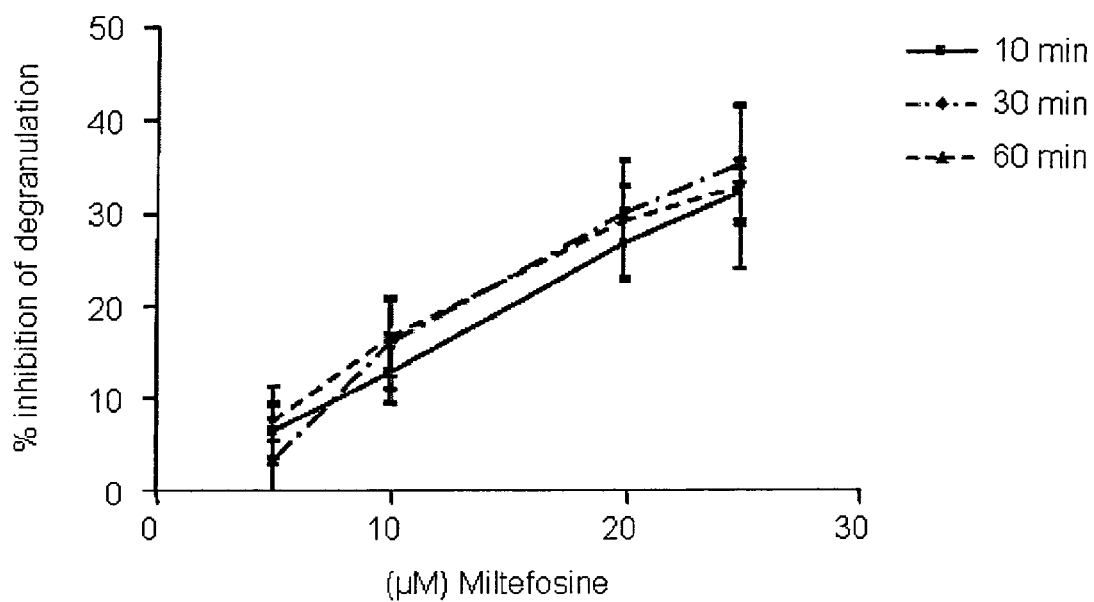
FIGS. 11 and 12 show the inhibitory effect of Miltefosine on the histamine release induced in primary human mast cells by anti-human-IgE and by Substance P, respectively.

Miltefosine inhibited IgE-induced histamine release in human mast cells dose-dependently with a maximal effect at 25 μM. The inhibitory effect of Miltefosine in human mast cells was not dependent on the pre-incubation time, i.e. even short pre-incubation times lead to the maximal inhibitory effect (35%) (FIG. 11).

Figure 12:
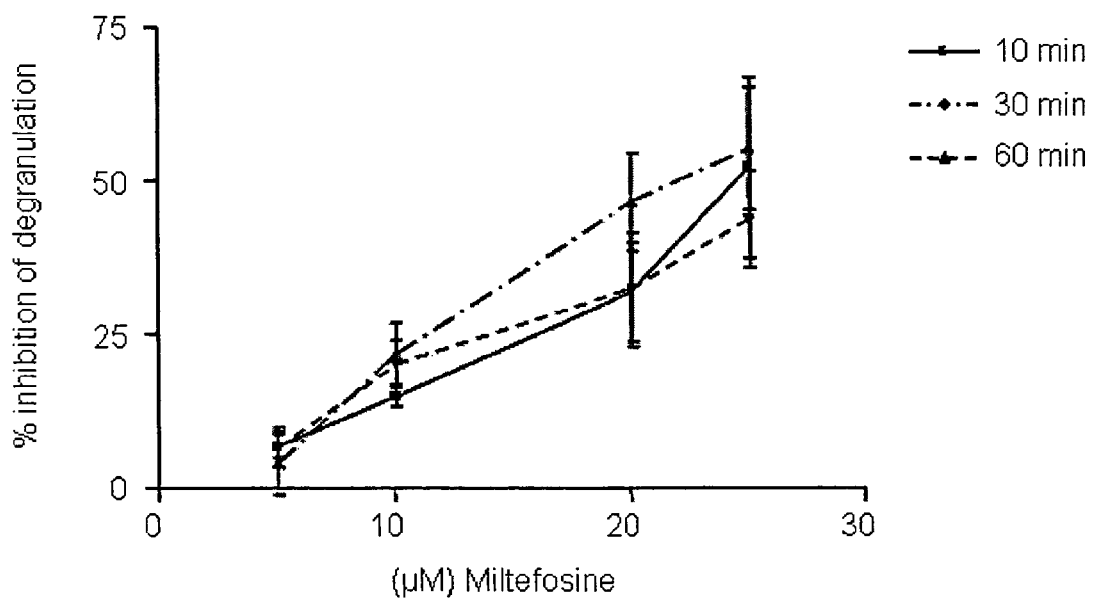

The inhibitory effect of Miltefosine on Substance P(SP) induced histamine release was similar to the effect on anti-IgE induced release. Miltefosine inhibited histamine release dose-dependently (45%), but as for IgE-induced histamine release was not dependent on pre-incubation time (FIG. 12).

Effect of Miltefosine on Histamine Release in Human Basophils

Figure 13:
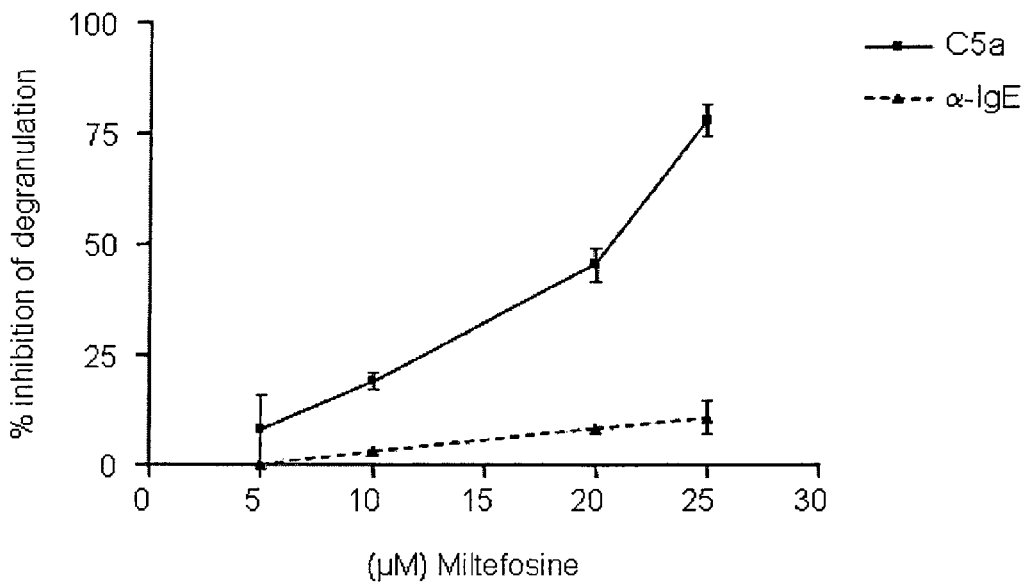
FIG. 13 shows the inhibitory effect of Miltefosine on the histamine release induced in human basophiles by C5a or by anti-human-IgE.
Figure 14:
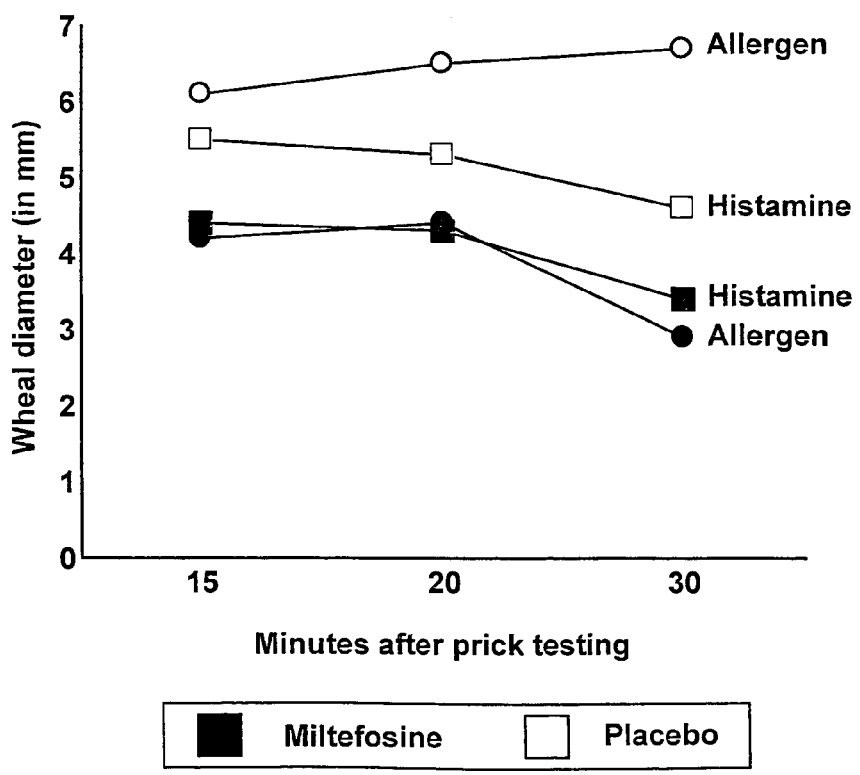
FIG. 14 shows wheal diameters at distinct time points after prick testing with histamine or patient-specific allergen in Miltefosine and placebo pre-treated skin.

Miltefosine inhibited anti-IgE induced histamine release in basophils dose dependently, but this effect was very small. Thus, the maximal inhibitory effect after 10 minutes pre-incubation amounted to just 10 percent using 25 μM Miltefosine. In contrast to the effects seen after anti-IgE stimulation, we observed a strong and significant inhibition of C5a-induced histamine release by 25 μM Miltefosine (75%) (FIG. 13).

In Vivo-experiments:

To assess the course of developing prick test lesions, wheal size was assessed macroscopically by measuring the diameters at distinct time points after prick testing. Interestingly, the sizes of wheals induced by allergen were markedly smaller in the regions that were pretreated with 6%-Miltefosine solution as compared to placebo (saline)-pretreated control areas. In addition, histamine-induced control wheals were also reduced, albeit to a lesser extent than allergen-induced wheals, at the Miltefosine-pretreated arm as compared to the saline-treated control arm (Table 4 and FIG. 7).

TABLE 4

Wheal analysis by macroscopic evaluation at different time points after prick testing in Miltefosine and placebo pre-treated skin.

| | Miltefosine pre-treatment | | placebo pre-treatment | | percent inhibition (by Miltefosine pre-treatment) | |
| --- | --- | --- | --- | --- | --- | --- |
| minutes after prick testing | allergen-prick wheal in mm ± standard error (n = 5) | histamine-prick wheal in mm ± standard error (n = 5) | allergen-prick wheal in mm ± standard error (n = 5) | histamine-prick wheal in mm ± standard error (n = 5) | allergen-prick % inhibition ± standard error (n = 5) | histamine-prick % inhibition ± standard error (n = 5) |
| 15 | 4.20 ± 1.36 | 4.40 ± 0.86 | 6.10 ± 1.33 | 5.50 ± 0.50 | 35.0 ± 16.6 | 22.4 ± 14.2 |
| 20 | 4.40 ± 1.34 | 4.30 ± 1.08 | 6.50 ± 1.44 | 5.30 ± 0.64 | 34.8 ± 18.0 | 19.2 ± 23.1 |
| 30 | 2.90 ± 1.36 | 3.40 ± 1.43 | 6.70 ± 1.59 | 4.60 ± 1.33 | 51.8 ± 22.8 | −7.9 ± 23.2 |

Discussion

Virtually all therapeutic interventions in mast cell-related diseases focus on the inhibition of histamine mediated processes by blocking the $H_1$-histamine receptor with anti-histamines. Inhibition of mast cell-degranulation is another interesting approach to control histamine and other mast cell-mediator related symptoms. However, up to now no agents with specific and effective mast cell-stabilizing properties have been identified. We show here, for the first time, that Miltefosine can inhibit the activation and degranulation of mast cells and basophils and that topical treatment with a 6% Miltefosine solution can inhibit IgE-dependent human mast cell stimulation in vivo. Most notably, the in vitro mast cell stabilizing effects of Miltefosine appear to not be limited to IgE-dependent activation and the in vivo suppressive effect was robust, i.e. detectable in all but one subject, and pronounced, i.e. stronger than what is to be expected for any mast cell-stabilizing agent described so far (e.g. cromoglycate). Interestingly, in vivo inhibitory effects of Miltefosine are also detectable, albeit to a smaller extent, in histamine induced wheal formation, suggesting that Miltefosine may block additional pro-inflammatory pathways.

The invention claimed is:

1. A method for the treatment and/or amelioration of an immunological disorder related to mast cell sensitization and/or activation comprising administration of a pharmaceutically active dose of a compound to a subject in need of such a treatment and/or amelioration wherein the compound is selected from edelfosine, miltefosine, perifosine and ilmofosine and further wherein the immunological disorder is atopic dermatitis.

2. The method of claim 1, wherein the compound of is miltefosine.

3. The method of claim 1 wherein said subject is a human subject.

* * * * *

UNITED STATES PATENT AND TRADEMARK OFFICE
CERTIFICATE OF CORRECTION

PATENT NO. : 7,998,945 B2  Page 1 of 1
APPLICATION NO. : 12/158615
DATED : August 16, 2011
INVENTOR(S) : Tobias Braxmeier, Tim Friedrichson and Gary Jennings It is certified that error appears in the above-identified patent and that said Letters Patent is hereby corrected as shown below:

ON THE TITLE PAGE

Please correct the application listed under the Foreign Application Priority Data Item (30): delete "05028388" and insert --05028388.6.--

The corrected Foreign Application Priority Data Item (30) should read:

Dec. 23, 2005   (EP)................................. 05028388.6

Signed and Sealed this
Twenty-ninth Day of November, 2011

David J. Kappos
*Director of the United States Patent and Trademark Office*